US008962581B2

(12) United States Patent
Kislin et al.

(10) Patent No.: US 8,962,581 B2
(45) Date of Patent: Feb. 24, 2015

(54) METHODS AND KITS TO IDENTIFY INVASIVE GLIOBLASTOMA

(75) Inventors: Kerri L. Kislin, Phoenix, AZ (US); Michael E. Berens, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 250 days.

(21) Appl. No.: 13/126,910

(22) PCT Filed: Oct. 29, 2009

(86) PCT No.: PCT/US2009/062645
§ 371 (c)(1),
(2), (4) Date: Aug. 12, 2011

(87) PCT Pub. No.: WO2010/059400
PCT Pub. Date: May 27, 2010

(65) Prior Publication Data
US 2012/0245045 A1    Sep. 27, 2012

Related U.S. Application Data

(60) Provisional application No. 61/109,581, filed on Oct. 30, 2008.

(51) Int. Cl.
C12N 15/113 (2010.01)

(52) U.S. Cl.
USPC .............. 514/44; 424/9.1; 424/9.2; 435/6.11; 435/7.92; 435/91.1; 435/91.31; 435/375; 536/23.1; 536/24.5

(58) Field of Classification Search
USPC .......... 435/6, 11, 7.92, 91.1, 91.31, 375, 455; 514/1, 2, 44; 536/23.1, 24.5, 24; 424/9.1, 9.2
See application file for complete search history.

(56) References Cited

U.S. PATENT DOCUMENTS

| 7,834,170 | B2 * | 11/2010 | Khvorova et al. | 536/24.5 |
| 7,933,733 | B2 * | 4/2011 | Ashrafzadeh et al. | 702/116 |
| 2007/0111244 | A1 | 5/2007 | Georges et al. | |
| 2009/0068669 | A1 * | 3/2009 | Georges et al. | 435/6 |
| 2010/0298360 | A1 * | 11/2010 | Belmares et al. | 514/267 |

FOREIGN PATENT DOCUMENTS

| WO | WO 0128577 A2 | 4/2001 |
| WO | WO 2005060996 A2 | 7/2005 |

OTHER PUBLICATIONS

Kislin et al., Proceedings of the American Association for Cancer Research Annual Meeting, Apr. 2008, vol. 49, pp. 283.*
Brada et al., Annals of Oncology, 2001, 12: 259-266.*
Morales et al., Proc Amer Assoc Cancer Res, 2005, vol. 46, Abstract #5477.*
Opalinska et al., Nature Rev., vol. 1, pp. 503-514 (2002).*
Jang et al., Expert Rev. Medical Devices, vol. 1, No. 1, pp. 127-138 (2004).*
Paroo et al., Trends in Biotech., vol. 22, No. 8, pp. 390-394 (2004).*
Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Doench et al., Genes & Development, vol. 18, No. 5, pp. 504-511 (2004).*
Holen et al., Nucleic Acids Res., vol. 30, No. 8, pp. 1757-1766 (2002).*
International Preliminary Report on Patentability for PCT application No. PCT/US09/062645 dated May 3, 2011.
International Search Report and Written Opinion of Searching Authority of PCT application No. PCT/US09/062645 dated Mar. 24, 2010.
Georgescu et al. Roles of NHERF1/EBP50 in Cancer. Curr Mol Med Sep. 2008 vol. 8, No. 6, pp. 459-468. Especially p. 465 right col. para 2.
GENBANK AF036241.1 Homo sapiens Na+/H+ exchange regulatory co-factor (NHERF) mRNA, complete cds. Oct. 27, 2000 [online] Available on the internet: <URL: http://www.ncbi.nlm.nih.gov/nuccore/2920584>, especially pp. 1,2.
Brdickova et al. Interaction between two adapter proteins, PAG and EBP50: a possible link between membrane rafts and actin cytoskeleton. FEBS Lett Oct. 26, 2001 vol. 507 No. 2 pp. 133-136. Especially p. 133 right col. para 4.
European Search Report and Opinion for application serial No. 09827986.2 dated Feb. 4, 2013.
Sah et al: "Therapeutic potential of RNA interference for neurological disorders", Life Sciences, Pergamon Press, Oxford, GB, vol. 79, No. 19, Oct. 4, 2006, pp. 1773-1780, XP028051112 ISSN: 0024-3205, DOI: 10.1016/J.LFS.2006.06.011 * p. 1779, left-hand column *.
Teresa Fanelli et al: "[beta]-Oestradiol rescues [delta] F508CFTR functional expression in human cystic fibrosis airway CFBE41o-cells through the up-regulation of NHERF1", Biology of the Cell, vol. 100, No. 7, Jul. 1, 2008, pp. 399-412, XP55045454, ISSN: 0248-4900, DOI: 10.1042/BC20070095 * figures 7-9*.
Omuro Antonio M P et al: "Lessons learned in the development of targeted therapy for malignant gliomas", Molecular Cancer Therapeutics, American Association of Cancer Research, US, vol. 6, No. 7, Jul. 1, 2007, pp. 1909-1919, XP002489046, ISSN: 1535-7163, DOI: 10.1158/1535-7163. MCT-07-0047 * this whole document *.
W P Roos et al: "Apoptosis in malignant glioma cells triggered by the temozolomide-induced DNA lesion 06-methylguanine", Oncogene, vol. 26, No. 2, Jan. 11, 2007, pp. 186-197, XP55045474, ISSN: 0950-9232, DOI: 10.1038/sj.onc.1209785 * the whole document *.

(Continued)

Primary Examiner — Jane Zara
(74) Attorney, Agent, or Firm — Rodney J. Fuller; Booth Udall Fuller

(57) ABSTRACT

The invention encompasses methods and kits used in the detection of invasive glioblastoma based upon the expression of NHERF-1. The methods and kits also allow prediction of disease outcome as well as therapeutic outcome.

12 Claims, 32 Drawing Sheets

(56) References Cited

OTHER PUBLICATIONS

M. Zheng et al: "Growth Inhibition and Radiosensitization of Glioblastoma and Lung Cancer Cells by Small Interfering RNA Silencing of Tumor Necrosis Factor Receptor-Associated Factor 2", Cancer Research, vol. 68, No. 18, Sep. 15, 2008, pp. 7570-7578, XP55045589, ISSN: 008-5472, DOI 10.1158/0008-5472.CAN-08-0632 *figure 1; table 1 *.

Kerri L Kislin et al: "NHERF-1: Modulator of Glioblastoma Cell Migration and Invasion", Neoplasia, vol. 11, No. 4, Apr. 1, 2009, pp. 377-387, XP055045373, DOI: 10.1593/neo.81572 * the whole document *.

* cited by examiner

```
                    30         SFVLNLGKDSNNLCLHFNPR          49
p15 peptides   75  EAVPFQPGSVAEVCITFDQANLIVKLPDGYEFK  108
Galectin-1    113        LNLEAINYMAADGDFK              128
```

IB: anti Galectin-1 → 
IP: anti NHERF-1

IB: anti NHERF-1 → 
IP: anti Galectin-1

METHODS AND KITS TO IDENTIFY INVASIVE GLIOBLASTOMA

CROSS-REFERENCE TO RELATED APPLICATIONS

This application is a National Phase filing of PCT Patent Application No. PCT/US2009/062645, filed on Oct. 29, 2009 which claims the benefit of U.S. Provisional Application 61/109,581, filed 30 Oct. 2008, that are incorporated by reference in their entireties.

STATEMENT REGARDING FEDERALLY SPONSORED RESEARCH

This invention was made with government support under NS042262 awarded by the National Institutes of Health. The government has certain rights in this invention.

INCORPORATION OF SEQUENCE LISTING

The entire contents of a paper copy of the "Sequence Listing" and a computer readable form of the sequence listing on diskette, containing the file named Seq_Listing2_ST25.txt, which is 7 kilobytes in size and was created on Apr. 18, 2013 are herein incorporated by reference. The support for the sequences can be found throughout the specification.

BACKGROUND OF THE INVENTION

Glioblastoma, also commonly referred to in the art as glioma or glioblastoma multiforme, is the most frequent form of primary brain cancer and has an average life expectancy from time of diagnosis of 9 months to one year. The highly lethal nature of this tumor partly originates from the invasive phenotype, which affords the tumor cells the ability to infiltrate adjacent brain tissues (See References 1 and 2.) In terms of eradicating this invasive disease, it is considered incurable using treatment modalities presently available. As a result, genes that drive the invasive behavior of glioblastoma are important diagnostic and prognostic markers of glioblastoma and are also markers for new treatment methods.

BRIEF SUMMARY OF THE INVENTION

The present invention provides among other things:
It is an object of the invention to detect invasive glioblastoma in a subject.
It is an object of the invention to visualize invasive glioblastoma cells.
It is an object of the invention to select a treatment on the basis of the presence of invasive glioblastoma.
It is an object of the invention to identify patients likely to respond to new glioblastoma therapeutics.
The above and other objects may be achieved using methods involving receiving a sample from a subject, adding a first reagent specific to NHERF-1 (alone or in combination with another marker) to a mixture that comprises the sample, and subjecting the mixture to conditions that allow detection of the binding of the reagent. The method may be used to assess the expression of NHERF-1 protein as a marker. The first reagent may comprise a first antibody. The first antibody may comprise a first label. The first label may be any label including one or more fluorescent compounds, one or more enzymes or one or more ligands any of which may be used alone or in combination with one or more additional labels. The method may further comprise adding a second antibody to the mixture that is capable of binding to the first antibody. The second antibody may comprise a second label. The second label may be any label. Examples include one or more fluorescent compounds, one or more enzymes, or one or more ligands, any of which may be used alone or in combination with one or more additional labels. Ligands may be any ligand, including biotin or streptavidin. The method may also be used to assess the expression of NHERF-1 mRNA or cDNA as a marker. In this case, the first reagent comprises a first nucleic acid. The first nucleic acid may be any nucleic acid capable of binding to NHERF-1 sequence. The method may further comprise adding a second nucleic acid to the mixture and subjecting the mixture to conditions that allow nucleic acid amplification. In this case, the first nucleic acid and the second nucleic acid are capable of hybridizing to separate sequences within NHERF-1 and further capable of hybridizing to separate strands of the cDNA. Either nucleic acid may hybridize to either strand—such as the first nucleic acid hybridizing to the 5'→3' strand and the second nucleic acid hybridizing to the 3'→5' strand. If the method comprises adding first and second nucleic acids, then the method may further comprise adding a third nucleic acid that comprises an oligonucleotide that is capable of hybridizing to part of the NHERF-1 sequence provided that the sequence that the third nucleic acid hybridizes to is between the sequences to which the first and second amino acids hybridize. The third nucleic acid may include a fluorescent compound. Any fluorescent compound may be used, including dR110, 5-FAM, 6FAM, dR6G, JOE, HEX, VIC, TET, dTAMRA, TAMRA, NED, dROX, PET, and LIZ. The method may further comprise methods that include DNA sequencing. The sample may be any sample. Some samples may include one or more cells. One example of such a sample is a brain biopsy. The method may further comprise collecting the sample from the subject. The method may further comprise correlating the presence of invasive glioblastoma with resistance of the glioblastoma to a glioblastoma therapeutic that targets non-migrating cells. While the therapeutic may be any therapeutic that targets non-migrating cells, examples include Temozolomide and bevacizumab. The reagent may be affixed to a solid substrate. The method may further comprise classifying the subject into a group on the basis of the binding of the reagent. In this example, the subject may be known to have glioblastoma. If the subject is known to have glioblastoma, the subject may be classified into a group that includes individuals that are likely to survive past a time period or the subject may be classified into a group that includes individuals likely to respond to a particular treatment.

The above and other objects may be achieved using kits that are used to detect the presence of invasive glioblastoma in a subject, comprising a first reagent capable of specifically binding to NHERF-1 and an indication of a level of expression of NHERF-1 that signifies the presence of invasive glioblastoma in the subject. The first reagent may comprise an antibody. That antibody may comprise a label. The label may be any label, including one or more fluorescent compounds, one or more enzymes, or one or more ligands either alone or in combination. The kit may also include a second antibody capable of binding to the first antibody. In this example, the second antibody may comprise a label. The label may be any label including one or more fluorescent compounds, one or more enzymes, or one or more ligands. The label may be any label including one or more fluorescent compounds, one or more enzymes or one or more ligands either alone or in combination. Both biotin and streptavidin may be considered ligands. The first reagent may comprise a first nucleic acid. The first nucleic acid may be any nucleic acid that binds specifically to NHERF-1. Such a kit may also include a second nucleic acid such as an oligonucleotide capable of hybridizing to part of NHERF-1 separate from where the first nucleic acid hybridizes and/or a third nucleic acid that hybridizes to NHERF-1 at sequence between the sequences to which the first and second nucleic acids hybridize. The third nucleic acid may comprise a fluorescent compound. The fluorescent compound may be any fluorescent compound including dR110, 5-FAM, 6FAM, dR6G, JOE, HEX, VIC, TET, dTAMRA, TAMRA, NED, dROX, PET, and LIZ. A kit comprising a first nucleic acid may also comprise an enzyme such as a DNA polymerase or reverse transcriptase. A kit comprising a first nucleic acid may have the first nucleic acid affixed to a solid substrate. An indication may be any indication of any level of expression of NHERF-1 that signifies the presence of invasive glioblastoma. The indication may be a positive control or physically included within the kit. The indication may comprise a writing. A writing may be made available on a website or it may comprise a photograph. The indication may also comprise software configured to detect the level of expression as input and identification of invasive glioblastoma as output. Such software may be incorporated into a machine that is configured to detect binding of a reagent to a marker.

The above and other objects may be achieved using methods involving detecting the presence of an invasive glioblastoma in a subject comprising: receiving a sample from the subject, assessing the expression of NHERF-1 in the sample, and comparing the expression of NHERF-1 in the sample to a level of expression predetermined to signify the presence of an invasive glioblastoma. Assessing the expression may comprise detecting the presence of NHERF-1 mRNA. While any method of detecting the presence of mRNA may be used, the method may include one or more of the following, alone or in combination: quantitative reverse transcriptase polymerase chain reaction, microarray analysis, and Northern Blot. Assessing the expression may comprise detecting the presence of NHERF-1 protein. While any way of detecting NHERF-1 protein may be used, the method may include one or more of the following, alone or in combination: enzyme linked immunosorbent assay, immunohistochemistry assay, high pressure liquid choromatography, mass spectrometry, and Western blot. The presence of an invasive glioblastoma may be further correlated with resistance of the glioblastoma to therapeutics that target non-migrating cancer cells including Temozolomide or bevacizumab.

BRIEF DESCRIPTION OF THE FIGURES

A more complete understanding of the present invention may be derived by referring to the detailed description when considered in connection with the following illustrative figures.

Figure 1:
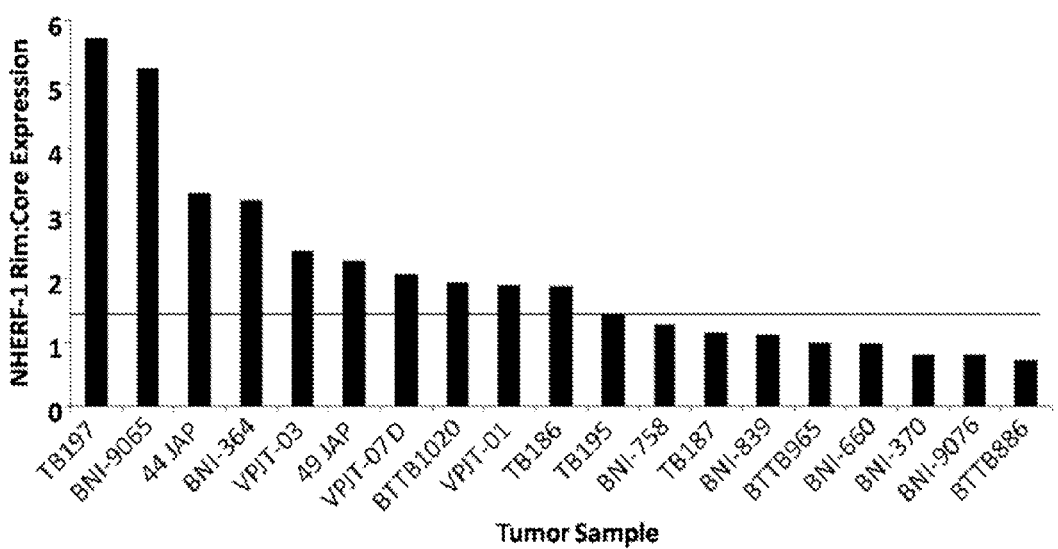
FIG. 1 depicts a graph showing the relative expression of NHERF-1 in cells collected from rim relative to cells collected from the core.

Elements and acts in the figures are illustrated for simplicity and have not necessarily been rendered according to any particular sequence or embodiment.

DETAILED DESCRIPTION OF THE INVENTION

Na+/H+ exchanger regulatory factor (NHERF-1) also known in the art as SLCA9A3R1 was initially recognized as a scaffolding protein that recruits membrane transporters/receptors and cytoplasmic signaling proteins into complexes localized at or near the plasma membrane in epithelial cells (See References 3 and 4). Specifically, NHERF-1 has been shown to regulate several G-protein coupled receptors, including the parathyroid hormone, the κ-opioid, and the β2-adrenergic receptors (See Reference 5). Moreover, NHERF-1 interacts with specific growth factor receptors such as the epidermal growth factor receptor and platelet-derived growth factor receptor and modulates mitogenic signaling by these receptor tyrosine kinases (See Reference 5). In addition, it contains two tandem PDZ domains (protein-binding domains conserved in the mammalian synaptic protein, PSD-95, *Drosophila* Dlg or discs large, and the adherens junction protein, ZO-1) that can oligomerize with other PDZ domains to enhance scaffolding activity (See References 6 and 7) as well as mediate other specific protein-protein interactions (See Reference 8). Previous studies have shown NHERF-1 to be upregulated in tumor tissue relative to its corresponding normal tissue in breast cancer (See Reference 3), schwannoma (See Reference 9) and in hepatocellular carcinoma (See Reference 10).

While these studies indicate that NHERF-1 plays a role in the progression of several cancer types, none have demonstrated conclusively the role of NHERF-1 in the pathogenesis of glioblastoma. Invasive cancer cells, including glioblastoma, are resistant to apoptosis (See References 11-16) However, decreasing the migratory capabilities of tumor cells can restore a certain level of sensitivity to cytotoxic insult (See References 15, 17). In a recent study, it was reported that NHERF-1 expression is found in varying amounts within regions of the normal rodent brain. Notably, neuronal elements (i.e. neuronal cell bodies visible in the granular layer of the dentate gyrus and the pyramidal cell bodies in the stratum pyramidale in the CA1 region of the hippocampus) did not contain NHERF-1, however, astrocytes surrounding such neurons were densely labeled (See Reference 30).

Furthermore, in a recent breast cancer study, MDA-MB-435 cells overexpressing NHERF-1 were shown to correlate with a hypoxic or serum-deprived tumor microenvironment and induce leading edge pseudopodia and corresponding redistribution of NHERF-1 to the pseudopodia tip Additionally, escaping MDA-MB-435 cells from tumor lobules contained in 3-D Matrigel culture revealed NHERF-1 disproportionately localized to the pseudopodial tip of the escaping and invading tumor cells, suggesting a role for NHERF-1 in tumor cell invasion (See Reference 31).

A major characteristic of glioblastoma is the propensity to invade and become resistant to chemotherapeutic agents (See References 15, 27, 32-36). A main cause of failure when treating with Temozolomide, (See Reference 37), is the ability of tumor cells to acquire resistance to apoptosis, which is necessary for tumor development and progression (See References 34, 38). The absence of apoptosis-resistance would otherwise induce tumor cell death when deprived of the support from neighboring cancer cells (See References 15, 34, 38).

The invention encompasses assessing the expression of a marker expressed by a glioblastoma cell in order to identify a cell as an invasive glioblastoma. The invention further encompasses assessing the expression of a marker to predict the risk of a patient diagnosed with glioblastoma to develop invasive glioblastoma. The invention also encompasses assessing the expression of a marker to identify a cell as a glioblastoma as opposed to another cell type.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms may be used interchangeably.

A marker may be represented by the sequence of one or more strands of a nucleic acid from which it may be derived. Examples of such nucleic acids include both single stranded and double stranded nucleic acid sequences including miRNA, tRNA, siRNA, mRNA, cDNA, or genomic DNA sequences including complimentary sequences. Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

Examples of molecules encompassed by a marker represented by a particular sequence or structure include nucleic acids or proteins that contain point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The following nonlimiting examples are included for the purposes of clarifying this concept: If expression of a specific marker in a sample is assessed by RTPCR, and if the sample expresses an mRNA sequence different from the sequence used to identify the specific marker by one or more nucleotides, but the marker may still be detected using RTPCR, then the specific marker encompasses the molecule present in the sample. Alternatively if expression of a specific marker in a sample is assessed by an antibody and the amino acid sequence of the marker in the sample differs from a sequence used to identify marker by one or more amino acids, but the antibody is still able to bind to the version molecule in the sample, then the specific marker encompasses the molecule present in the sample.

Expression encompasses any and all processes through which material derived from a nucleic acid template may be produced. Expression thus includes processes such as RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material whether in vitro, in vivo, or ex vivo. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, direct sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatography, HPLC, mass spectrometry, protein microarray analysis, PAGE analysis, isoelectric focusing, 2-D gel electrophoresis, or any enzymatic assay.

Other methods used to assess expression include the use of natural or artificial ligands capable of specifically binding a marker. Such ligands include antibodies, antibody complexes, conjugates, natural ligands, small molecules, nanoparticles, or any other molecular entity capable of specific binding to a marker. Antibodies may be monoclonal, polyclonal, or any antibody fragment including an Fab, $F(ab)_2$, Fv, scFv, phage display antibody, peptibody, multispecific ligand, or any other reagent with specific binding to a marker. Ligands may be associated with a label such as a radioactive isotope or chelate thereof, dye (fluorescent or nonfluorescent,) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Differential expression encompasses any detectable difference between the expression of a marker in one sample relative to the expression of the marker in another sample. Differential expression may be assessed by a detector, an instrument containing a detector, or by aided or unaided human eye. Examples include but are not limited to differential staining of cells in an IHC assay configured to detect a marker, differential detection of bound RNA on a microarray to which a sequence capable of binding to the marker is bound, differential results in measuring RTPCR measured in $\Delta Ct$ or alternatively in the number of PCR cycles necessary to reach a particular optical density at a wavelength at which a double stranded DNA binding dye (e.g. SYBR Green) incorporates, differential results in measuring label from a reporter probe used in a real-time RTPCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

The expression of the marker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a marker. Examples include but are not limited to the identity of a cell as a particular cell including a particular normal or cancer cell type, the likelihood that one or more diseases is present or absent, the likelihood that a present disease will progress, remain unchanged, or regress, the degree to which a disease will respond or not respond to a particular therapy. Further examples include the likelihood that a cell will move, senesce, apoptose, differentiate, metastasize, or change from any state to any other state or maintain its current state.

Expression of a marker in a sample may be more or less than that of a level predetermined to predict the presence or absence of a cellular or physiological characteristic. The expression of the marker in the sample may be more than $1,000,000\times$, more than $100,000\times$, more than $10,000\times$, more than $1000\times$, more than $100\times$, more than $10\times$, more than $5\times$, more than $2\times$, about $1\times$, more than $0.5\times$, more than $0.1\times$ more than $0.01\times$, more than $0.001\times$, more than $0.0001\times$, more than $0.00001\times$, more than $0.000001\times$, more than $0.0000001\times$ or less than $0.0000001\times$ that of a level predetermined to predict the presence or absence of a cellular or physiological characteristic.

The invention contemplates assessing the expression of the marker in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression that signifies a physiological or cellular characteristic may be assessed by any of a number of methods. The skilled artisan will understand that numerous methods may be used to select a level of expression for a particular marker or a plurality of markers that signifies a particular physiological or cellular characteristic. In diagnosing the presence of a disease, a threshold value may be obtained by performing the assay method on samples obtained from a population of patients having a certain type of disease (cancer for example,) and from a second population of subjects that do not have the disease. In assessing disease outcome or the effect of treatment, a population of patients, all of which have, a disease such as cancer, may be followed for a period of time. After the period of time expires, the population may be divided into two or more groups. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the marker in a sample is more similar to the predetermined expression of the marker in one group relative to the other group, the sample may be assigned a risk of having the same outcome as the patient group to which it is more similar.

In addition, one or more levels of expression of the marker may be selected that provide an acceptable ability of its ability to signify a particular physiological or cellular characteristic. Examples of such characteristics include identifying or diagnosing a particular disease, assessing a risk of outcome or a prognostic risk, or assessing the risk that a particular treatment will or will not be effective.

For example, Receiver Operating Characteristic curves, or "ROC" curves, may be calculated by plotting the value of a variable versus its relative frequency in two populations. For any particular marker, a distribution of marker expression levels for subjects with and without a disease may overlap. This indicates that the test does not absolutely distinguish between the two populations with complete accuracy. The area of overlap indicates where the test cannot distinguish the two groups. A threshold is selected. Expression of the marker in the sample above the threshold indicates the sample is similar to one group and expression of the marker below the threshold indicates the sample is similar to the other group. The area under the ROC curve is a measure of the probability that the expression correctly indicated the similarity of the sample to the proper group. See, e.g., Hanley et al., *Radiology* 143: 29-36 (1982).

Additionally, levels of expression may be established by assessing the expression of a marker in a sample from one patient, assessing the expression of additional samples from the same patient obtained later in time, and comparing the expression of the marker from the later samples with the initial sample or samples. This method may be used in the case of markers that indicate, for example, progression or worsening of disease or lack of efficacy of a treatment regimen or remission of a disease or efficacy of a treatment regimen.

Other methods may be used to assess how accurately the expression of a marker signifies a particular physiological or cellular characteristic. Such methods include a positive likelihood ratio, negative likelihood ratio, odds ratio, and/or hazard ratio. In the case of a likelihood ratio, the likelihood that the expression of the marker would be found in a sample with a particular cellular or physiological characteristic is compared with the likelihood that the expression of the marker would be found in a sample lacking the particular cellular or physiological characteristic.

An odds ratio measures effect size and describes the amount of association or non-independence between two groups. An odds ratio is the ratio of the odds of a marker being expressed in one set of samples versus the odds of the marker being expressed in the other set of samples. An odds ratio of 1 indicates that the event or condition is equally likely to occur in both groups. An odds ratio grater or less than 1 indicates that expression of the marker is more likely to occur in one group or the other depending on how the odds ratio calculation was set up. A hazard ratio may be calculated by estimate of relative risk. Relative risk is the chance that a particular event will take place. It is a ratio of the probability that an event such as development or progression of a disease will occur in samples that exceed a threshold level of expression of a marker over the probability that the event will occur in samples that do not exceed a threshold level of expression of a marker. Alternatively, a hazard ratio may be calculated by the limit of the number of events per unit time divided by the number at risk as the time interval decreases. In the case of a hazard ratio, a value of 1 indicates that the relative risk is equal in both the first and second groups; a value greater or less than 1 indicates that the risk is greater in one group or another, depending on the inputs into the calculation.

Additionally, multiple threshold levels of expression may be determined. This can be the case in so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk of a disease developing or signifying a physiological or cellular state. A risk may be assigned based on which "bin" a test subject falls into.

A subject includes any human or non-human mammal, including for example: a primate, cow, horse, pig, sheep, goat, dog, cat, or rodent, capable of developing cancer including human patients that are suspected of having endometrial cancer, that have been diagnosed with cancer, or that have a family history of cancer. Methods of identifying subjects suspected of having cancer include but are not limited to: physical examination, family medical history, subject medical history, endometrial biopsy, or a number of imaging technologies such as ultrasonography, computed tomography, magnetic resonance imaging, magnetic resonance spectroscopy, or positron emission tomography.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The present invention further provides kits to be used in assessing the expression of a RNA in a subject to assess the risk of developing disease. Kits include any combination of components that facilitates the performance of an assay. A kit that facilitates assessing the expression of a microRNA may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu, reverse transcriptase, or other, and/or reagents that facilitate nucleic acid amplification. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A specific nucleic acid may include a label. A label may be any substance capable of aiding a machine, detector, sensor, device, or enhanced or unenhanced human eye from differentiating a sample that that displays positive expression from a sample that displays reduced expression. Examples of labels include but are not limited to: a radioactive isotope or chelate thereof, a dye (fluorescent or nonfluorescent,) stain, enzyme, or nonradioactive metal. Specific examples include but are not limited to: fluorescein, biotin, digoxigenin, alkaline phosphatase, biotin, streptavidin, 3H, 14C, 32P, 35S, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, and LIZ.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may assume a circular or other two dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence.

In some aspects of the invention, the probe may be affixed to a solid substrate. In other aspects of the invention, the sample may be affixed to a solid substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate in the case of a Southern Blot.

Kits may also contain reagents that detect proteins, often through the use of an antibody. These kits will contain one or more specific antibodies, buffers, and other reagents configured to detect binding of the antibody to the specific epitope. One or more of the antibodies may be labeled with a fluorescent, enzymatic, magnetic, metallic, chemical, or other label that signifies and/or locates the presence of specifically bound antibody. The kit may also contain one or more secondary antibodies that specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody. Such a kit may also contain enzymatic substrates that change color or some other property in the presence of an enzyme that is conjugated to one or more antibodies included in the kit.

A kit may also contain an indication of a level of expression that signifies a particular physiological or cellular characteristic. An indication includes any guide to a level of expression that, using the kit in which the indication is provided, would signal the presence or absence of any physiological or cellular state that the kit is configured to detect. The indication may be expressed numerically, expressed as a color, expressed as an intensity of a band, derived from a standard curve, or derived from a control. The indication may be printed on a writing that may be included in the kit or it may be posted on the internet or embedded in a software package.

One aspect of the invention encompasses screens that identify inhibitors of NHERF-1. This aspect of the invention encompasses inhibitors of cell migration activity as well as inhibitors of NHERF-1 effector recruitment activity. Inhibition encompasses any action that hinders, from any detectable level up to and including complete inactivation, the progression of a biological process. Such biological processes include expression of a gene or activities of a gene product, progression of a disease, normal and abnormal metabolic activities, interactions between entities within an organism, or interactions between one organism and another. Further nonlimiting examples of biological processes include development, death, maturation, infection, pain, apoptosis, or homeostasis. Inhibition includes actions that silence or repress the expression of a gene. Inhibition also includes actions that hinder the activity of the RNA product, protein product, or postranslationally modified protein product of a gene. Inhibition may be effectuated through a single agent that inactivates a single gene or gene product, by a single agent that inactivates a combination of more than one gene or gene product, a combination of agents that inactivates a single gene or gene product or a combination of agents that inactivates a combination of more than one gene or gene product.

Inhibition may be effectuated directly by an agent that directly causes the inhibition of a biological process or by agents that trigger one or more different biological processes to effectuate the inhibition of the first biological process. Agents that cause inhibition may also be called inhibitors. Examples of inhibitors include compositions such as compounds that trigger RNAi silencing such as microRNA or siRNA, small molecular compounds, proteins such as soluble receptors or antibodies or any fragment thereof, including an Fab, F(ab)$_2$, Fv, scFv, Fc, phage display antibody, peptibody or any other composition of matter that may inactivate or hinder a biological process. Further nonlimiting examples of inhibitors include X-rays, UV rays, visible light including laser light, and sound.

Cell migration activity includes any mode through which a cell may move in two-dimensional or three-dimensional space. Such migration includes movement through the use of pseudopodia including the adhesion of pseudopodia to a surface, a flagellum, a cilium, acts of amoeboid movement, extravasation, myosin-actin interactions, microtubule extension, or any other process through which a cell moves itself from one place to another or changes its morphology. In one aspect of the invention, cell migration activity is measured through cell adhesion. Using adhesion, cell migration activity may be measured by cell-cell aggregation, monolayer radial migration, including adhesion to a cell matrix comprising laminin, BSA or any other cell matrix component, three dimensional spheroid dispersion, or any other method that measures adhesion based cellular migration in space. Migration activity may be measured by any method that detects that a cell has moved from one place to another or has changed its morphology. Such methods include flow cytometry, capillary electrophoresis, visual examination by light, fluorescence, or electron microscopy, or any such method known in the art or yet to be developed. Inhibitors of cell migration activity are agents that disrupt any molecular or cellular process involved in cell migration activity.

Effector recruitment activity includes any activity of a protein that contributes to the formation of a complex of two or more molecules that serves to catalyze one or more chemical reactions. Effectors include any protein, nucleic acid or other molecule that may be included in a complex that performs one or more biological activities. Recruitment activity encompasses any protein-protein interaction including phosphorylation, dephosphorylation and other enzymatic activities, adhesion, signaling cascades, and cytokine/chemokine interactions, any protein-nucleic acid interactions, such as any of those involved in transcription, translation or DNA replication, or any other process that includes a protein interacting with another molecule. NHERF-1 displays effector recruitment activity in that it is involved in the formation of a complex from cytoplasmic signaling proteins and membrane receptors/transporters. Effectors of NHERF-1 include Galectin-1, focal adhesion kinase (FAK), THO complex subunit 4 (THOC4), NAD, Sideroflexin-1, 14-3-3 protein epsilon, Syntenin-1, DPYSL3 protein, GARS protein, and CTTN Src substrate cortactin. Inhibitors of effector recruitment activity encompass any compound that disrupts effector recruitment activity. Inhibitors of NHERF-1 effector recruitment activity may disrupt the interaction of NHERF-1 with any of the proteins listed above, the interaction between any of those proteins with each other, and further includes any members of a NHERF-1 complex that might be later identified.

In one aspect of the invention, inhibitors of effector recruitment activity may be identified on the basis of their ability to disrupt the binding of NHERF-1 to one or more of its effectors. This specific binding may be measured by any method that allows the measurement of a protein-protein interaction known in the art. Such method include the following examples, alone or in combination as necessary: co-immunoprecipitation, biomolecular fluorescence complementation, fluorescence resonance energy transfer, label transfer, a yeast two-hybrid screen, in-vivo crosslinking, tandem affinity purification, chemical crosslinking, quantitative immunoprecipitation combined with knock-down (QUICK), dual polarization interferometry, protein-protein docking, static light scattering, immunoprecipitation plus mass-spectrometry, Strep-protein interaction experiment (SPINE), surface plasmon resonance, fluorescence correlation spectroscopy, or any other method of measuring the specific interaction between one protein and another now known in the art or yet to be disclosed.

In another aspect of the invention a glioblastoma patient is treated by first assessing the expression of NHERF-1 and then treating with an effective dose of a NHERF-1 inhibitor, potentially in combination with Temozolimide. The effective dose of a compound is that amount effective to prevent occurrence of the symptoms of a disorder or to treat some symptoms of the disorder from which the patient suffers. Effective dose also includes an effective amount, a therapeutic amount, or any amount sufficient to elicit the desired pharmacological or therapeutic effects, thus resulting in effective prevention or treatment of the disorder. Thus, when treating a patient with glioblastoma, an effective amount of compound is an amount sufficient to slow, or arrest the progression, migration, metastasis, growth, or development of the tumor with the result that life is extended. Prevention includes a delay in onset of symptoms. Treatment includes a decrease in the symptoms associated with the disorder or an amelioration of the recurrence of the symptoms of the disorder. A pharmacologically acceptable dose encompasses any dose that may be administered to a patient that will not be lethal to the patient or cause effects that threaten the health or the life of the patient.

Patients include any human being, nonhuman primate, companion animal, or mammal suffering from a disease. In one aspect of the invention, the patient has symptoms that signify the presence of a tumor or other growth in the brain. Such symptoms include headache, seizures, mental or personality changes, mass effect, or one of a number of focal or localized systems including ringing or buzzing sounds, hearing loss, loss of coordination, reduced sensation, weakness or paralysis, difficulty with walking or speech, difficulty keeping balance, decreased muscle control, or double vision. Patients may display one or more different brain tumor types including acoustic neurinoma, astrocytoma, ependyoma, glioblastoma multiforme, meningioma, metastatic tumors originating from another tumor type, mixed glioblastoma, oligodendroglioblastoma, or pineal region tumor.

Where clinical applications are contemplated, it will be necessary to prepare pharmaceutical compositions that comprise expression vectors, virus stocks, proteins, antibodies or drugs in a form appropriate for the intended application. In many instances, this will entail preparing compositions that are essentially free of pyrogens, as well as other impurities that could be harmful to humans or animals. A pharmaceutical composition includes an active component such as Temozolomide, a NHERF-1 inhibitor or other compound and a pharmacologically acceptable carrier. Pharmaceutically acceptable carriers include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic or prophylactic compositions is contemplated. Supplementary active ingredients also can be incorporated into the compositions.

Pharmaceutical compositions include classic pharmaceutical preparations. Administration of these compositions according to the present invention will be via any common route so long as the marker tissue is available via that route. This includes oral, nasal, buccal, rectal, vaginal or topical. Alternatively, administration may be by orthotopic, intradermal, subcutaneous, intramuscular, intraperitoneal intratumoral, circumferentially, catheterization, or intravenous injection. Such compositions would normally be administered as pharmaceutically acceptable compositions. In some aspects of the invention, the pharmaceutical composition is formulated in such a way that it is capable of crossing the blood-brain barrier. However, in other aspects of the invention, the pharmaceutical composition may be administered directly to a tumor or placed in close proximity to a tumor.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

Herein Inventors establish that NHERF-1 identifies invasive cells in cancer. Inventors further establish that inhibition of NHERF-1 activity in glioblastoma cell lines reduces migration and dispersion responses. Inventors finally establish that inhibition of NHERF-1 activity renders glioblastoma cell lines sensitive to Temozolamide treatment.

EXAMPLE 1

Elements and acts in the example are intended to illustrate the invention for the sake of simplicity and have not necessarily been rendered according to any particular sequence or embodiment. The example is also intended to establish possession of the invention by the Inventors.

Paired glioblastoma subpopulations, were isolated either from the tumor core or the invasive rim, from 19 patient tumors. Gene expression profiling, followed by fold change analysis, resulted in a list of differentially expressed genes. NHERF-1 was among the genes expressed in both the tumor core and the invasive glioblastoma cells located at the tumor rim. Expression profiling was performed using 44K Agilent Human Whole Genome oligo microarray chips and then confirmed with quantitative reverse transcription-PCR (QRT-PCR). In 10 of 19 glioblastoma core and rim biopsies, samples of cells invading at the rim showed 1.5- to nearly 6-fold greater expression compared with cells taken from the core. Referring now to FIG. 1: In 19 independent glioblastoma specimens, 1000-2000 stationary (core) and invasive (rim) cells were harvested by laser-capture microdissection and analyzed on a microarray. In the graph, relative NHERF-1 mRNA signal intensity is expressed as a ratio of expression of NHERF1 in rim relative to expression of NHERF-1 in core. These findings establish that expression of NHERF-1 can both identify glioblastoma cells as invasive glioblastoma and predict migratory activity of glioblastoma.

Figure 2:
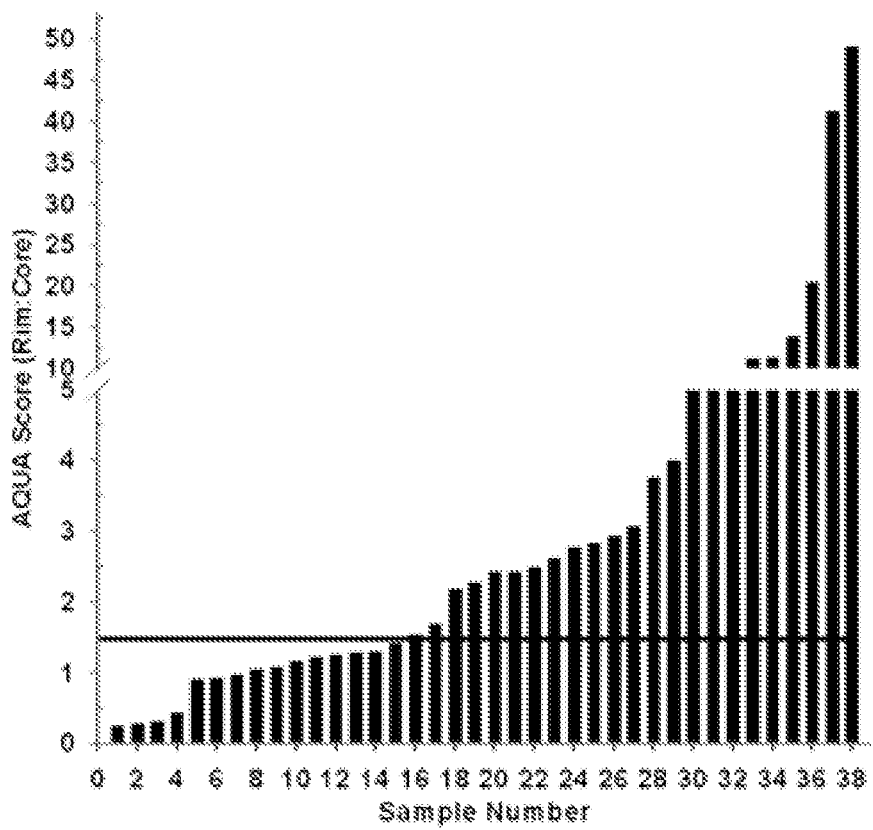
FIG. 2 depicts AQUA scores of NHERF-1 protein in matched rim and core samples for each listed specimen.
Figure 3:
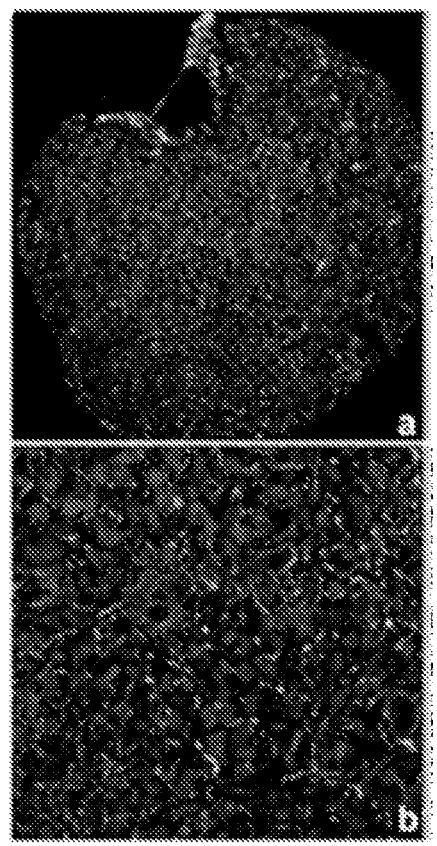
FIG. 3 depicts a paraffin section of tumor core from a selected sample.
Figure 4:
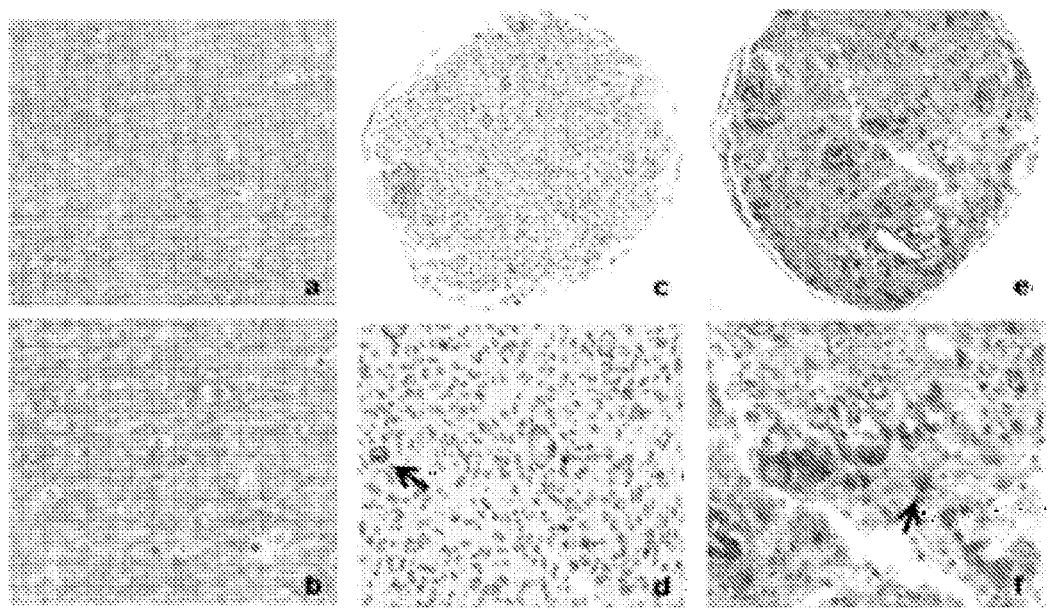
FIG. 4 depicts paraffin sections of tumor free non-neoplastic brain, glioblastoma core, and invasive rim.

NHERF-1 protein expression in a series of glioblastoma specimens, was assessed on a tissue microarray consisting of 38 tumor cases containing core and rim was examined. A set of algorithms known as automated quantitative analysis (AQUA) was used to assess immunofluorescence on the tissue microarrays (See Reference 23). Solely for the purposes of this assay a level of NHERF-1 signifying identification of a cell as an invasive glioblastoma includes an AQUA score greater than 1. AQUA scores greater than 1 were observed in the invasive rim compared to the core in 31 out of 38 cases. Referring now to FIG. 2: AQUA scores of NHERF-1 protein levels were measured in matched sets of rim:core for each tumor with the ratio of AQUA scores for each specimen plotted from lowest AQUA score to highest. Samples with an AQUA score fold difference above '1' were identified as invasive. In FIG. 3, a paraffin section of tumor core from a selected sample was stained with a fluorescently labeled monoclonal antibody specific to NHERF-1 and analyzed by an imaging system. The top panel depicts 10× magnification and the bottom panel depicts 20× magnification. In FIG. 4, typical paraffin sections of tumor-free non-neoplastic brain (a,b), glioblastoma core (c,d) and invasive rim (e,f) from tissue microarray immunostained against NHERF-1 are shown. Panels a, c, and e are 10× magnified and panels b, d, and f are 20× magnified. Arrows indicate representative NHERF-1 positive staining AQUA scoring of NHERF-1 expression of the tissue microarray resulted in the following scores:

| IHC Score | Core | Edge/Rim |
| --- | --- | --- |
| 1 | 12.1% (n = 6) | 1.7% (n = 1) |
| 2 | 42.4% (n = 14) | 29.3% (n = 17) |
| 3 | 39.3% (n = 13) | 69.0% (n = 40) |

NHERF-1 expression may be assessed by DAB-1HC staining of NHERF-1. Expression that identifies a cell as an invasive glioblastoma, solely for the purposes of this assay is a score of 2 or more while a score of 1 or less indicates that the cell is not an invasive glioblastoma. Of 33 GBM cores, 27 had a score of 2 or more (81.8%) and 6 had a score less than 1 (18.2%). Of 58 GBM rims, 57 had a score of 2 or more (98.2%) and had a score of 1 or less (1.7%). No scores of two or more were seen in negative control non-neoplastic autopsy brain samples.

Figure 5:
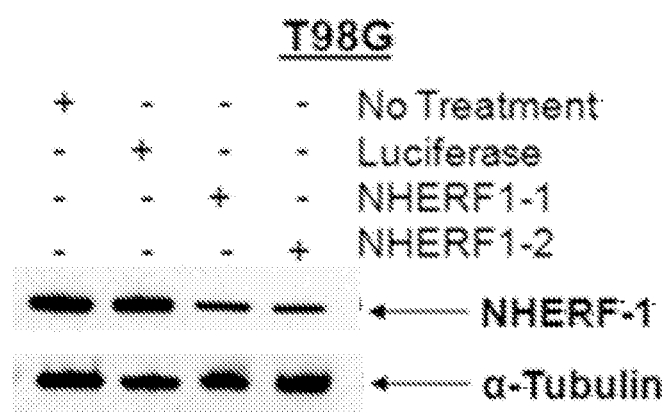
FIG. 5 depicts a decrease in NHERF-1 protein expression in T98G cells transfected with NHERF-1 siRNA.
Figure 6:
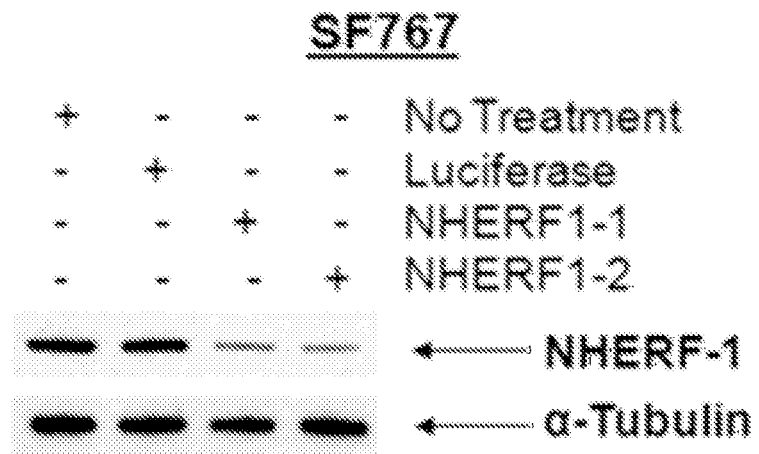
FIG. 6 depicts a decrease in NHERF-1 protein expression in SF767 cells transfected with NHERF-1 siRNA.

Two independent sequences of siRNA configured to silence NHERF-1 transfected into the glioblastoma derived T98G and SF767 cell lines. Endogenous expression of NHERF-1 was assessed in both cell lines by Western blot relative to a luciferase transfected negative control. NHERF-1 mRNA was inhibited by approximately 60-90% by both siRNAs. FIGS. 5 and 6 show reduced NHERF-1 expression in T98G and SF767 transfected with NHERF-1 siRNA.

Figure 7:
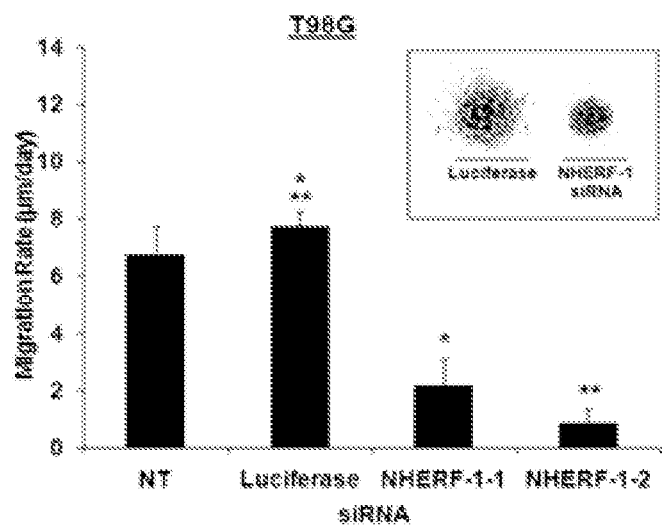
FIG. 7 depicts a decrease in T98G migration in a radial migration assay when the cells are transfected with NHERF-1 siRNA.
Figure 8:
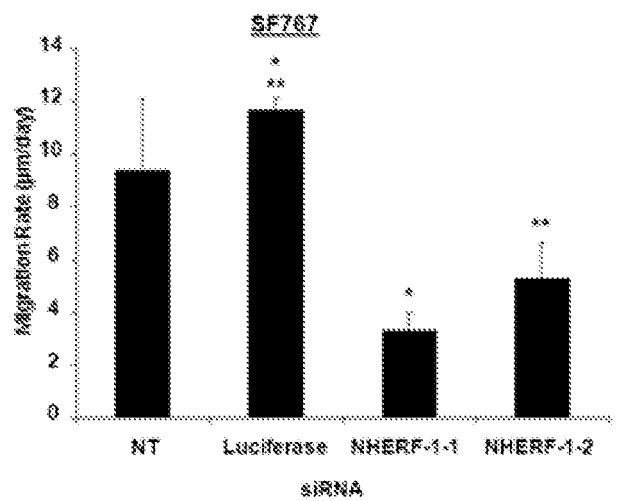
FIG. 8 depicts a decrease in SF767 migration in a radial migration assay when the cells are transfected with NHERF-1 siRNA.

FIG. 7 shows that migration of T98G cells is inhibited when the cells are transfected with NHERF-1 siRNAs. FIG. 8, shows that migration of SF767 cells is inhibited when the cells are transfected with NHERF-1 siRNA's. Results shown are those of a radial migration assay. The bars represent the average of 5±SEM from three independent experiments. For T98G cells, single asterisk (*) indicates p<0.01 comparing luciferase-treated T98G cells to NHERF-1-1 treated cells, and double asterisks (**) indicate p<0.01 comparing luciferase-treated cells to NHERF1-2 siRNA treated cells. For SF767 cells, a single asterisk (*) indicates p<0.001 comparing luciferase-treated cells to NHERF-1-1 treated cells, and double asterisks (**) indicate p<0.001 comparing luciferase-treated cells to NHERF-1-2 treated cells; (two-tailed student t-test).

Figure 9:
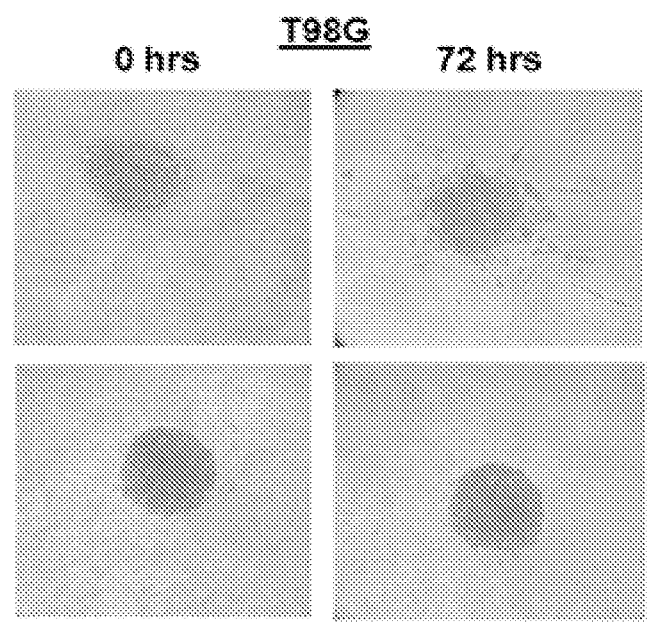
FIG. 9 depicts inhibition of dispersion of T98G cells from a multicellular spheroid in a collagen matrix when the cells are transfected with NHERF-1 siRNA.
Figure 10:
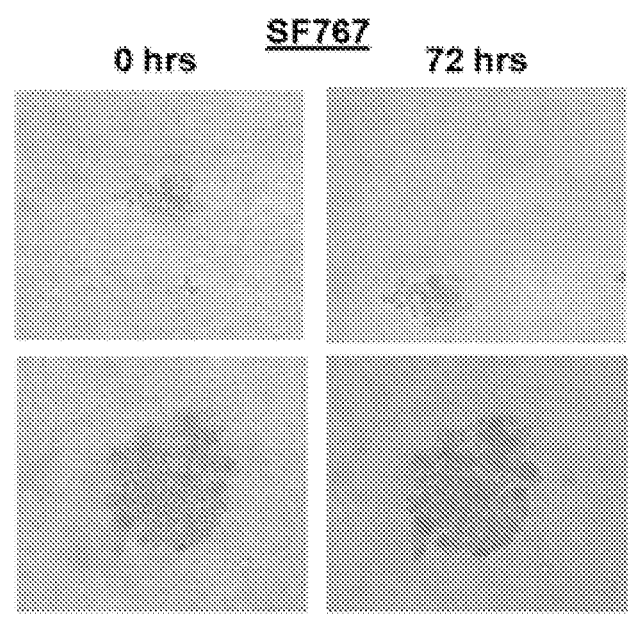
FIG. 10 depicts formation of large spheroids by SF767 cells in a collagen matrix when the cells are transfected with NHERF-1 siRNA.

FIG. 9 shows that dispersion of T98G cells from multicellular spheroid in 1% collagen is inhibited when NHERF-1 is depleted. The upper left panel indicates luciferase-transfected spheroid at time zero. The upper right panel indicates luciferase-transfected spheroid after 72 hours. The lower left panel indicates NHERF-1 siRNA-transfected spheroid at 0 hour, and the lower right panel indicates NHERF-1 siRNA-transfected spheroid after 72 hours. FIG. 10 shows that treatment with NHERF-1 siRNA results in the formation of large spheroids by SF767 cells in a 1% collagen culture. The upper left panel indicates luciferase-transfected spheroid at 0 hour and the upper right panel indicates luciferase-transfected spheroid after 72 hours. The lower left panel indicates NHERF-1 siRNA (combination of the two sequences)-transfected spheroid at 0 hour, and the lower right panel indicates luciferase-transfected spheroid at 72 hours. Images shown are representative of 3 independent experiments.

Monolayer radial migration assays revealed that inhibition of NHERF-1 expression in T98G and SF767 glioblastoma cells induced a significant decrease in migration rates.

| T98G Cells: Migration Rate (μm/day) | | | |
| --- | --- | --- | --- |
| | siRNA Transfected | | |
| | NHERF 1-1 | NHERF-1-2 | Mock Transfected |
| Mean | 2.2 | 0.82 | 7.7 |
| Standard Dev | 0.94 | 0.53 | 0.53 |
| P-value relative to mock | P < 0.01 | P < 0.01 | NA |

| SF767 Cells: Migration Rate (μm/day) | | | |
| --- | --- | --- | --- |
| | siRNA Transfected | | |
| | NHERF 1-1 | NHERF-1-2 | Mock Transfected |
| Mean | 3.3 | 5.2 | 11.6 |
| Standard Dev | 0.65 | 1.4 | 0.46 |
| P-value relative to mock | P < 0.001 | P < 0.001 | NA |

That inhibition of NHERF-1 causes a lack of cell dispersion of T98G cells relative to mock-transfected cells was further established using cell spheroids propagated three-dimensionally in collagen I gel (FIG. 9). Moreover, inhibition of NHERF-1 in SF767 cells resulted in tight and robust spheroid formations. Note that SF767 are typically incapable of spheroid formation and dispersion in collagen I gel (FIG. 10).

Figure 11:
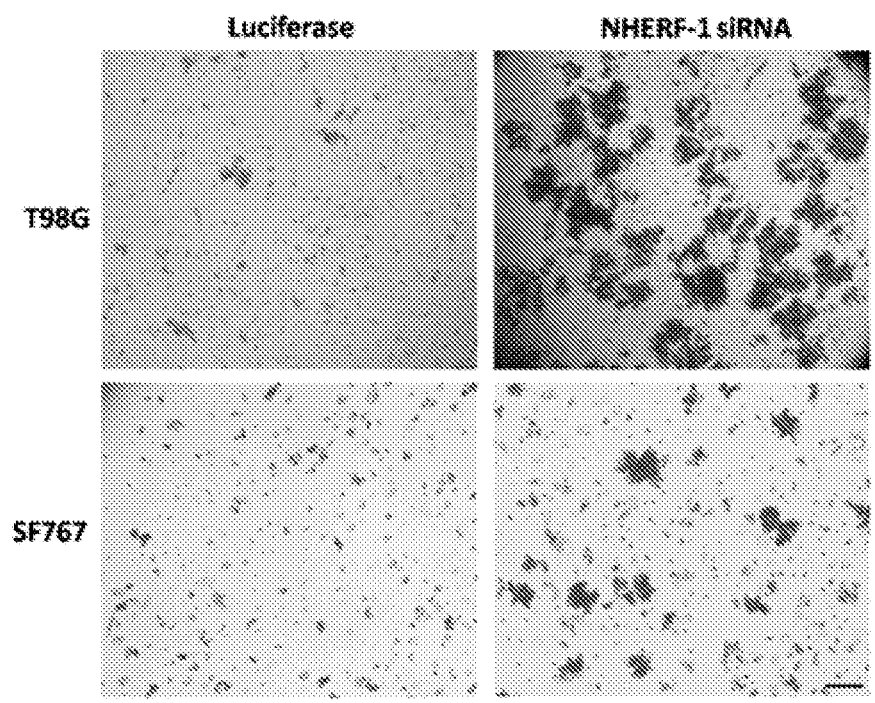
FIG. 11 depicts the formation of aggregates by T98G and SF767 cells when the cells are transfected with NHERF-1 siRNA.
Figure 12:
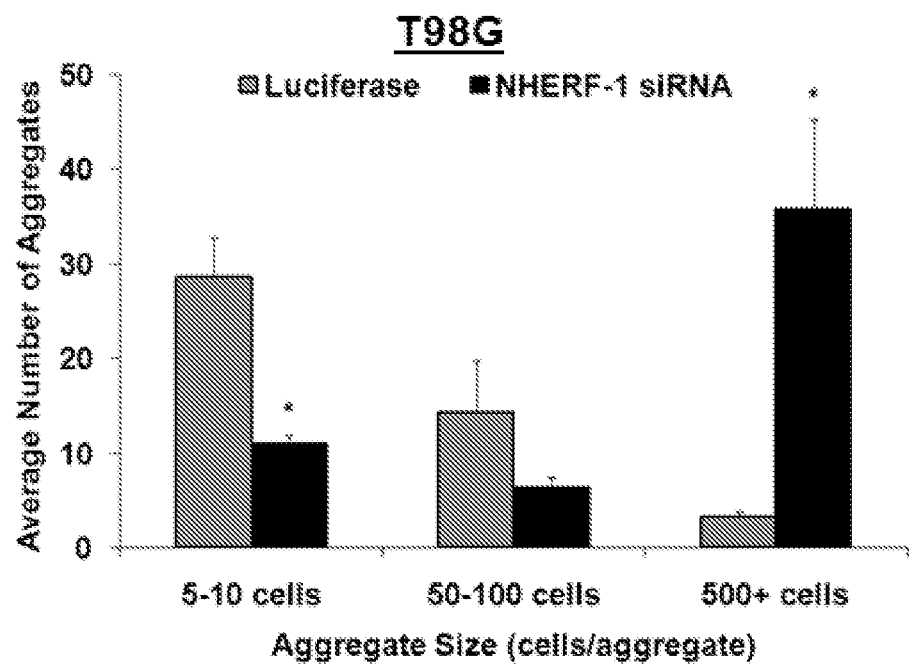
FIG. 12 depicts the distribution of aggregates formed by T98G cells when transfected with NHERF-1 siRNA compared to a control.
Figure 13:
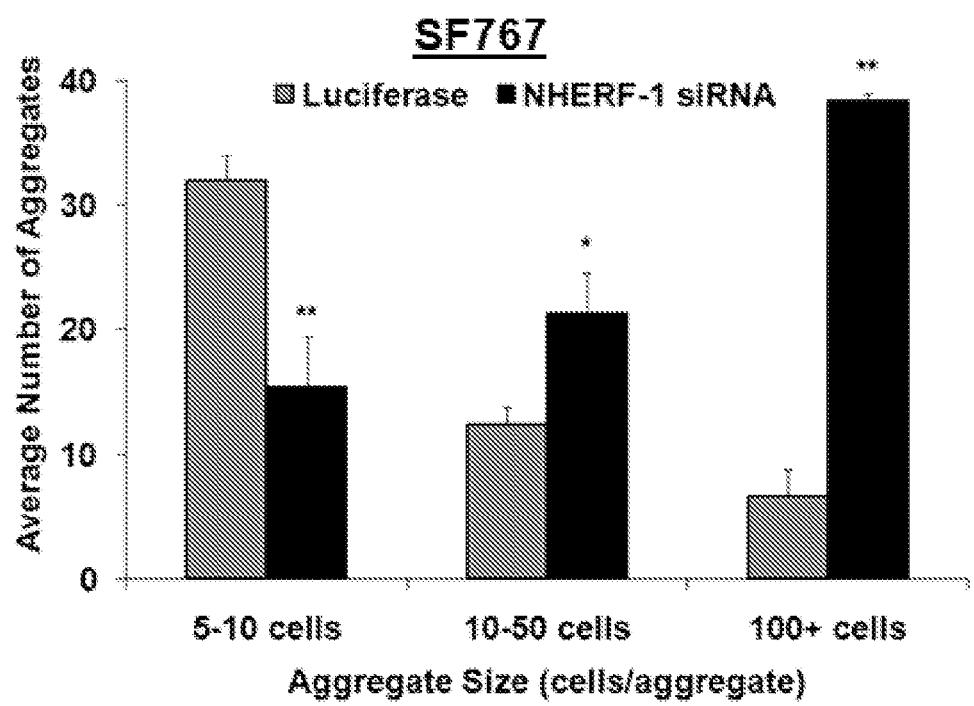
FIG. 13 depicts the distribution of aggregates formed by SF767 cells when transfected with NHERF-1 siRNA compared to a control.

When NHERF-1 is inhibited, T98G and SF767 glioblastoma cell lines displayed greater cell-cell adhesion, via aggregate formation, compared to control cells treated with luciferase siRNA. Referring now to FIG. 11-13, inhibition of expression of NHERF-1 by siRNA results in increased glioblastoma cell line aggregation. FIG. 11 shows phase-contrast photomicrographs of T98G and SF767 cells treated with NHERF-1 siRNA or luciferase siRNA (control). These results indicate that inhibition of NHERF-1 expression causes glioblastoma cells to aggregate. In 12 and 13, T98G and SF767 cell suspensions (respectively) were scored visually for aggregated cells following 60 minutes in culture. The bars represent the average number of cell aggregates following NHERF-1 siRNA. The values represent the mean and standard deviation from three randomly selected fields. *, p<0.03; **, p<0.01, when comparing NHERF-1 siRNA-treated cell aggregates with corresponding luciferase-transfected control cell aggregates (two-tailed student t-test).

Average Number of Each Size Aggregate in T98G Cells (Mean±SD)

| | Aggregate Size | | |
| --- | --- | --- | --- |
| siRNA | 5-10 | 50-100 | 500+ |
| NHERF-1 | 11.00 ± 1.00 | 6.33 ± 1.15 | 35.67 ± 9.61 |
| Luciferase | 28.67 ± 4.16 | 14.33 ± 5.51 | 3.33 ± 0.58 |
| P-value | P < 0.03 | | P < 0.03 |

Average Number of Each Sized Aggregate in SF767 Cells (Mean±SD)

| siRNA | Aggregate Size | | |
|---|---|---|---|
| | 5-10 | 50-100 | 100+ |
| NHERF-1 | 15.33 ± 4.04 | 21.33 ± 3.21 | 38.33 ± 0.58 |
| Luciferase | 32.00 ± 2.00 | 12.33 ± 5.51 | 6.67 ± 2.08 |
| P-value | P < 0.01 | P < 0.03 | P < 0.01 |

Moreover, when NHERF-1 expression was inhibited, the T98G and SF767 showed a significant increase in cell-cell matrix adhesion compared to control cells treated with luciferase plated on either BSA or laminin.

Cell-Cell Matrix Adhesion T98G Cells (Mean±SD)

| siRNA | Matrix | |
|---|---|---|
| | BSA | Laminin |
| NHERF-1 | 0.351 ± 0.066 | 0.526 ± 0.041 |
| Luciferase | 0.227 ± 0.013 | 0.265 ± 0.015 |
| P-value | P < 0.05 | P < 0.001 |

Cell-Cell Matrix Adhesion SF767 Cells (Mean±SD)

| siRNA | Matrix | |
|---|---|---|
| | BSA | Laminin |
| NHERF-1 | 0.266 ± 0.022 | 0.427 ± 0.072 |
| Luciferase | 0.171 ± 0.017 | 0.191 ± 0.008 |
| P-value | P < 0.005 | P ≤ 0.005 |

These findings suggest that when NHERF-1 is inhibited in cells, said cells are unable to disperse from a multicellular spheroid and cells undergo a phenotypic switch causing an increase in cell-cell cohesion, likely due to the expression of one or more cell adhesion molecules.

Figure 14:
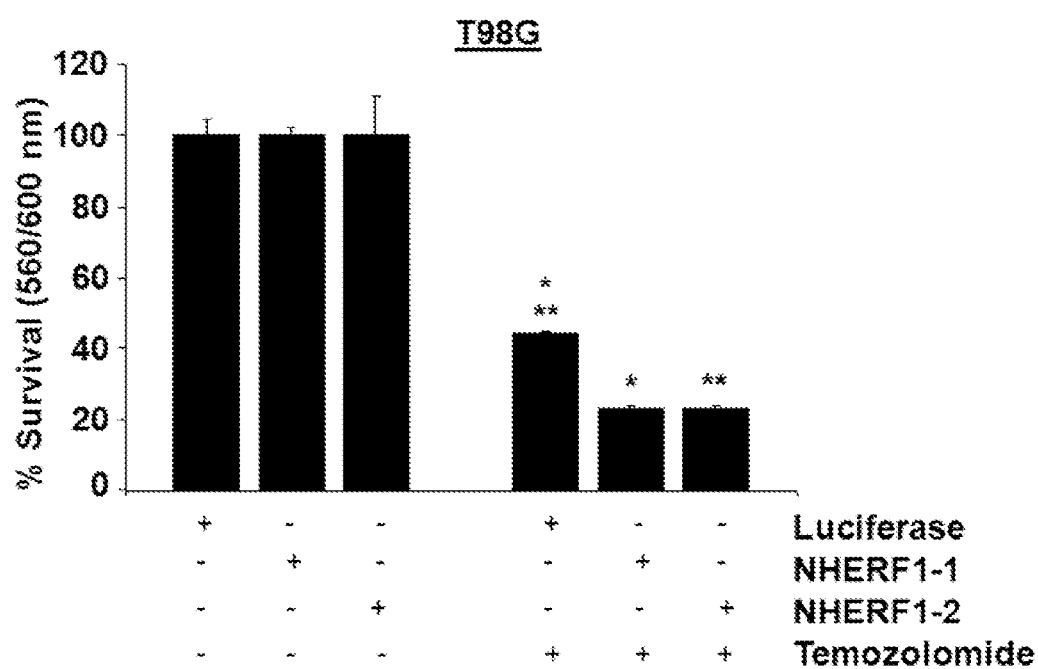
FIG. 14 depicts increased sensitivity to Temozolomide of T98G cells transfected with NHERF-1 siRNA relative to a control.
Figure 15:
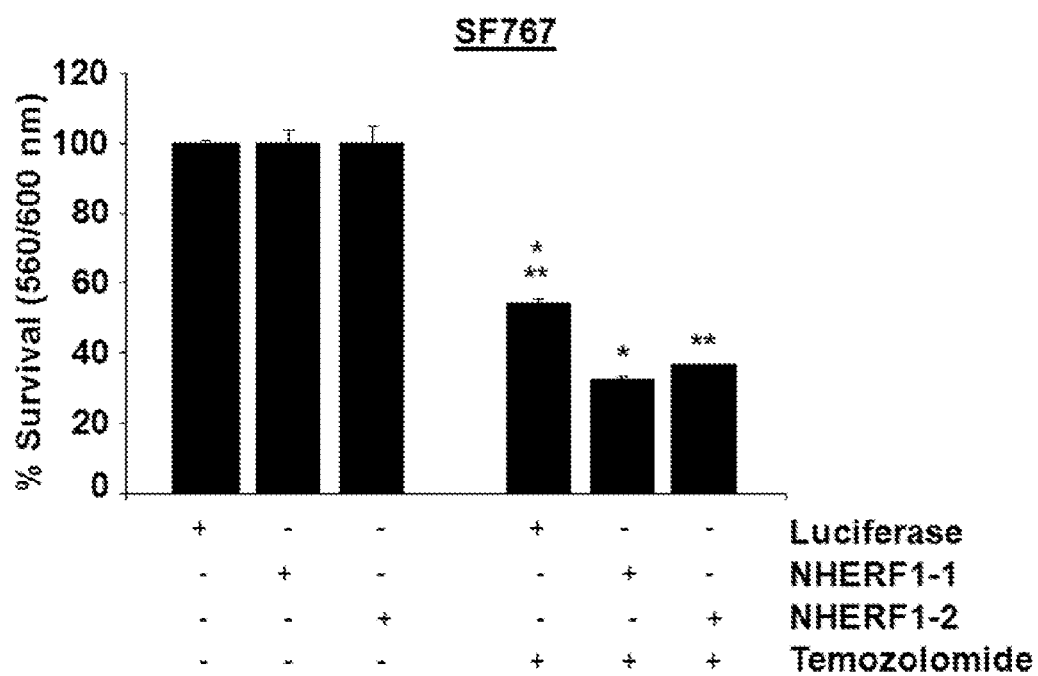
FIG. 15 depicts increased sensitivity to Temozolomide of SF767 cells transfected with NHERF-1 siRNA relative to a control.
Figure 16:
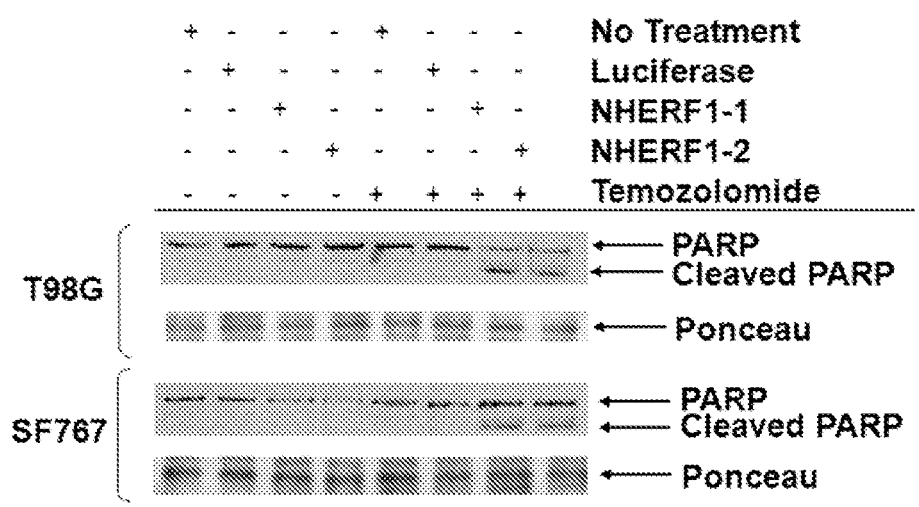
FIG. 16 depicts increased PARP-1 cleavage in Temozolomide treated T98G and SF767 cells that were transfected with NHERF-1 siRNA relative to a control.

GBM sensitivity to Temozolomide treatment was evaluated following knockdown of NHERF-1. Referring now to FIGS. 14-16: the inhibition of NHERF-1 expression renders T98G and SF767 cells sensitive to Temozolomide. In 14 and 15, T98G and SF767 cells (respectively) were treated for 48 hours with NHERF-1 siRNA concurrently with either 250 μM or 125 μM Temozolomide. The bars represent the percent of cells surviving treatment normalized to the percent of cells surviving in a control that did not contain Temozolomide. Values represent mean and standard deviation from three independent experiments. A single asterisk (*) indicates p<0.01 comparing luciferase-treated T98G cells to NHERF-1-1 treated T98G cells, and double asterisks (**) indicate p<0.01 comparing luciferase-treated T98G cells to NHERF-1-2 treated T98G cells; For SF767 cells, a single asterisk (*) indicates p<0.001 comparing luciferase-transfected cells treated with Temozolomide to NHERF-1-1-transfected cells treated with Temozolomide, and double asterisks () indicate p<0.001 comparing luciferase-transfected cells treated with Temozolomide to NHERF-1-2-transfected cells treated with Temozolomide; (two-tailed student t-test). Data are representative of two independent experiments, each run with triplicate samples. In FIG. 16**, Western blot analysis to determine PARP cleavage is depicted. T98G and SF767 glioblastoma cells were untreated, transfected with luciferase, or transfected with NHERF-1-1 or NHERF-1-2 siRNA with or without Temozolomide. After 24 hours, whole cell lysates were prepared and immunoblotted for whole and cleaved PARP. Ponceau staining was used as a loading control. Data are representative of two independent experiments.

% Survival±% Standard Deviation

| siRNA | Cell Line | |
|---|---|---|
| | T98G | SF767 |
| NHERF-1-1 + TMZ | 23.17 ± 0.967 | 23.38 ± 0.948 |
| Luciferase + TMZ | 54.37 ± 1.18 | 54.37 ± 1.18 |
| P-value | P < 0.001 | P < 0.001 |

| siRNA | Cell Line | |
|---|---|---|
| | T98G | SF767 |
| NHERF-1-2 + TMZ | 23.38 ± 0.948 | 36.77 ± 0.235 |
| Luciferase + TMZ | 54.37 ± 1.18 | 54.37 ± 1.18 |
| P-value | P < 0.001 | P < 0.001 |

Inhibition of NHERF-1 also caused a higher level of Temozolomide-induced apoptosis. Western blot analysis of PARP cleavage following 24 hours of TMZ treatment showed that T98G and SF767 glioblastoma cell lines manifest minimal levels, if any, of PARP cleavage when untreated, treated with luciferase or in the presence of NHERF-1 siRNA alone. However, when both cell lines were treated with NHERF-1 siRNA in combination with Temozolomide for 24 hours, there was a pronounced increase in the levels of PARP cleavage compared to cells treated with Temozolomide alone, or in combination with luciferase siRNA. See FIG. 5C.

The following non-limiting examples of methods are intended solely for the purpose of illustration and example.

Cell Culture Conditions and Extracellular Matrix (ECM) Preparation. Human GBM cell lines SF767 (See Reference 18) and T98G (were maintained in minimum essential medium supplemented with 10% heat-inactivated fetal bovine serum in a 37° C., 5% $CO_2$ atmosphere at constant humidity.

Clinical Samples and Histology. Human glioblastoma tumor samples were obtained from patients who underwent primary therapeutic subtotal or total tumor resection performed under image guidance. All specimens (19 in number) were collected and submitted to the study under institutional review board-approved protocols. No chemotherapy or radiotherapy was performed on the patients prior to resection. The samples, which were obtained from the main tumor mass and the invasive rim, were immediately frozen on dry ice to be used in laser capture microdissection (LCM). Another portion was fixed in paraformaldehyde and paraffin-embedded for histologic evaluation. Histologic diagnosis was made by standard light microscopic evaluation of hematoxylin and eosin-stained sections. All tumor samples were classified as WHO grade IV GBM (See reference 19.)

Laser Capture Microdissection. LCM was performed as described previously (See References 20-22, incorporated by reference in their entireties.) Briefly, 1000-2000 tumor core and invasive rim cells were dissected from 8-μm sections cut from four flash-frozen glioblastoma (WHO grade IV) tumors. Cells in the tumor core were identified and captured; tumor cells immediately adjacent to necrotic areas, cortical areas, cells with small, regular nuclei, or that evidenced features of endothelial and blood cells were avoided. White matter-invading GBM cells were identified through their nuclear atypia and heteropyknotic staining, which was consistent with that of the cells within the tumor core. Reactive astrocytes were discriminated through their distinct star-like morphology with eosinophilic cytoplasm and large, acentric, round nuclei, and were avoided.

RNA Isolation and Amplification. Total RNA was isolated from LCM cells listed above and quantified by real-time reverse transcription polymerase chain reaction (RT-PCR). This consisted of performing RT-PCR with Histone 3A primers using a serial dilution of cDNA of known concentrations as standards. The remaining RNA (approximately 10 ng) was amplified in two rounds with an RNA Amplification kit, yielding between 30 and 60 ng of copy RNA.

cDNA Microarray Analysis: The amount and quality of RNA preparations were evaluated. The LCM RNA samples were hybridized to 44K human whole genome oligo microarrays. Methods used in microarray hybridization and washing were as described in manufacturer's protocol. Hybridized DNA microarrays were scanned with a resolution of 5 μm and TIFF images were processed to measure intensity values. Each gene's measured intensity was divided by its control channel value in each sample; if the control channel was below 10 then 10 was used instead. If the control channel and the signal channel were both below 10 then no data was reported. There is a per chip normalization to the $50^{th}$ percentile of all measurements in that sample. The percentiles of all of the chips were calculated using genes marked present. Each gene was divided by the median of its measurements in all samples. If the median of the raw values was below 10 then each measurement for that gene was divided by 10 if the numerator was above 10, otherwise the measurement was discarded.

Tissue Microarray (TMA). Five-micron sections from a glioblastoma invasion tissue microarray consisting of 35 WHO grade-IV glioblastoma specimens (See Reference 22) were subjected to the described staining methods using the NHERF-1 antibody. The fluorescence-based automated and quantitative analysis (AQUA) system (See References 23 and 24) automatically identified and measured alterations in the expression of NHERF-1 within the tissue spots of the TMA. Patient information corresponding to the glioblastoma samples on the tissue microarray is available through an online database (available at the World Wide Web: illumine.5amsolutions.com.

Immunohistochemistry (IHC)-Fluorescence Staining. The TMA slide was baked at 65° C. for one hour. The slide was de-paraffinized in three xylene washes (2 minutes each) followed by a dehydration series of 100% ethanol, 95% ethanol, 70% ethanol and water (20 dips each). The slide was then placed on an autostainer. The slide was blocked and antigens were retrieved using a sodium citrate based buffer pH 6.5 for 20 minutes. The primary monoclonal antibody, anti-NHERF-1 EPB-10, was diluted 1:100 and incubated for 30 minutes. For fluorescent staining, rabbit anti-Glial Fibilary Acidic Protein (GFAP) was used to stain the cyctoplasmic portions of glial cells. A secondary antibody cocktail containing anti-rabbit Alexa 555 and anti-mouse-HRP was incubated for 30 minutes. Lastly, a tyramide signal amplification system using Cy5 was used to stain the primary marker NHERF-1. The slide was coverslipped using a solution containing DAPI. For IHC staining, the slide was incubated with secondary antibody conjugated to HRP for 30 minutes followed by a DAB (diaminobenzidine) substrate. The slide was counterstained with hematoxylin and coverslipped for imaging.

Image Acquisition and Analysis. Automated and quantitative analysis (AQUA) permitted automated high-throughput quantification of biomarkers (See references 23 and 25, incorporated by reference in their entireties). Multiple, monochromatic, high-resolution (2048×2048 pixels) images were obtained from each TMA spot with an epifluorescence microscope (See Reference 24). AQUA scores/units for NHERF-1 were then calculated that correspond to the average signal intensity divided by locale area. This information was then exported in a format suitable for analysis by standard software packages. Further scoring by a pathologist of NHERF-1 levels on the TMA was performed using a system for chromophore to capture the outcome: 1, negative to very weak; 2, moderate; 3, intense staining.

siRNA Preparation and Transfection: The siRNA oligonucleotide specific for GL2 luciferase was previously described (See Reference 26, incorporated by reference in its entirety). The siRNA oligonucleotides specific for NHERF-1 were designed and validated. siRNA sequences to NHERF-1 isoforms used were: NHERF-1-1(regions 494-514, 5'-CT-GCGGAATGGATCACACTGA-3'; SEQ ID NO. 7) and NHERF-1-2 (regions 2631-2651, 5'-AACTCATTGGGT-CAGCAATTA; SEQ ID NO. 8). Transient transfection of siRNA was carried out using a transfection reagent. Cells were plated in a 60 mm plate at $8.0 \times 10^5$ cells/plate in 3 ml of DMEM, supplemented with 10% serum without antibiotics. Transfections were carried out after cells were fully adherent (6 hours post-plating). Cells were infected with NHERF-1 siRNA oligonucleotides or control GL2 luciferase siRNA oligonucleotides at a concentration of 20 nM for 16 hours. No cell toxicity was observed at this concentration of siRNA. Cells were assayed on day 3 or day 4 post-transfection.

Western Blot Analysis: Immunoblotting and protein determination experiments were preformed as previously described (See Reference 27.) Monolayers of cells were washed in phosphate buffered saline (PBS) containing 1 mM phenylmethylsulfonyl fluoride (PMSF) and then lysed in 2× sodium dodecyl sulfate (SDS) sample buffer (0.25 M Tris-HCl, pH 6.8, 2% SDS, and 25% glycerol) containing 10 μg/ml aprotinin, 10 μg/ml leupeptin and 1 mM PMSF. Protein concentrations were determined using a BCA assay with bovine serum albumin as a standard. Twenty-five micrograms of total cellular protein was loaded per lane, separated by 10% SDS polyacrylamide gel electrophoresis (PAGE) and then transferred to nitrocellulose by electroblotting. The nitrocellulose membrane was blocked with 5% nonfat dry milk in Tris-buffered saline (pH 8.0) with 0.1% Tween-20 prior to addition of the primary antibody and then HRP-conjugated anti-mouse/rabbit IgG. Bound secondary antibodies were detected using a chemiluminescence system. A mouse monoclonal antibody to NHERF-1 (EPB-10) was obtained and utilized at a concentration of 1:1000. The rabbit polyclonal antibody to PARP was used at a concentration of 1:1000.

Radial Cell Migration Assay: Quantification of cellular migration was performed using a microliter scale migration assay as described previously (See Reference 27.) 10-well slides were coated with 10 μg/ml of human laminin at 37° C. for 1 hour and washed with PBS to enhance cell attachment, without promoting migration. Approximately 2000 cells were plated onto each well of slides using a cell sedimentation manifold to establish a confluent 1 mm diameter monolayer. Those cells under siRNA conditions were treated in monolayer prior to transfer into manifolds. Cells were allowed to disperse for 24 to 48 hours. Measurements were taken of the area occupied by the cells at regular intervals over 48 hours. The average migration rate of 5 replicates was calculated as the increasing radius of the entire cell population over time.

Three-Dimensional Spheroid Dispersion Assay: Spontaneous multicellular spheroids, derived from T98G and SF767 cells, were sandwiched between 10 μl collagen I gel below spheroid and 25 μl collagen I gel on top of spheroid supplemented with MEM, 2% fetal bovine serum in each well of a 384-well plate and overlain with 20 µl MEM, 10% fetal bovine serum. 18 hours post implantation, dispersion assays were monitored up to 72 hours. Hanging drop culture (See Reference 28) was used for all subsequent spheroid production where $2 \times 10^5$ cells/ml for T98G and SF767 lines were seeded in 20 µl droplets and cultured over a water-filled dish for 4 days. Those cells under siRNA conditions were treated in monolayer prior to the formation of hanging drops.

Cell-Cell Adhesion Assay: Cells were grown to 75% confluency, treated with NHERF-1 siRNA or luciferase control overnight, media was changed and the cells were allowed to recover for 24 hours. The cells were washed with calcium/magnesium-free PBS and detached from the culture dishes with 4 mM EDTA in calcium/magnesium-free PBS to preserve cell surface expression of cadherin subtypes. Cells were separated to a single cell suspension by trituration with a Pasteur pipette. After centrifugation the cells were suspended in a final concentration of 0.5 million cells/ml in calcium-free suspension modified Eagle's medium in the absence of serum, and $10^6$ cells were maintained in suspension on 1 mg/ml poly-2-hydroxyethyl methacrylate (Sigma) coated 35-mm$^2$ culture dishes to prevent cell attachment. Images were taken of at least three fields per well following 60 minutes in culture. Cell aggregates were counted based on the number of cells per aggregate.

Cell Viability Assay. The Alamar Blue assay was used to assess viability as described previously (See Reference 29, incorporated by reference in its entirety). Briefly, 4000 cells of each population were seeded in quadruplicate wells of 96-well plastic plates in 200 µl of culture medium supplemented with 10% fetal bovine serum. Cells were treated with various conditions and the assay was developed 48 hours later. Alamar Blue was then added to the cells in a volume of 20 µl (10% of total volume) per well and the plates were incubated for 6 hours at 37° C. The plates were read on a fluorescence plate reader (excitation, 560 nm; emission, 600 nm). Averages of the fluorescence values were calculated and normalized to controls without Temozolomide. $IC_{50}$ values for Temozolomide were 250 µM for the T98G and 125 µM for the SF767 line.

EXAMPLE 2

Uncontrolled cell proliferation and wide dispersion characterize glioblastoma multiforme (GBM). Tyrosine kinase receptors and downstream signaling pathways play crucial roles in both tumor migration and proliferation. As with many tumors, a temporal dichotomy between growth and invasion is evident, however, key intracellular factors responsible for regulating the 'switch' between proliferation and migration remain poorly discerned. The purpose of this study was to interrogate in human GBM specimens, cellular mechanisms controlling the invasive phenotype. In a GBM expression array database of 19 human tumor samples, Na+/H+ exchanger regulatory factor 1 (NHERF-1) proved to be significantly overexpressed in the invading rim of the tumor specimens when compared to matched, more proliferative, core regions. In this example it is disclosed that NHERF-1 acts as a 'switch' for GBM cells in the differential adoption of a migratory versus proliferative phenotype. In addition, NHERF-1 and Grb2 compete for binding to EGFR, the consequence of which modifies intracellular signaling to favor either migration or proliferation, respectively. When GBM cells are placed on GBM-derived ECM, supports cell motility, NHERF-1 effectively binds to and co-localizes with galectin-1, a protein known to signal through FAK. Overexpression of NHERF-1 in GBM cells results in diminished proliferation accompanied by decreased MAPK signaling and increased cell invasion. Furthermore, by reducing MAPK signaling through knockdown of Grb2, GBM cells manifest a migratory phenotype. These findings depict NHERF-1 as a novel molecular switch that regulates the dichotomy between the migratory and proliferative phenotypes in GBM.

Defining characteristics of nearly all cancers, including glioblastoma mutliforme (GBM) (See Reference 42), are uncontrolled cell proliferation and migration/invasion into surrounding tissue. These behaviors develop as a consequence of aberrant extracellular and intracellular signaling pathways that control division and migration. Inappropriate trans-membrane growth factor receptor signaling, by overproduction of growth factor, receptor mutation or dysfunctional downstream circuits consequent to loss of inhibitory feedback, each may play a role in the transformation of normal cells to cancer. Intracellular signaling involving tyrosine kinase growth factor receptors, such as epidermal growth factor receptor (EGFR), occurs in close proximity to the receptor itself and involves activation of a small GTP-binding protein (RAS) through the adapter molecule growth factor receptor-bound protein-2 (Grb2) and a guanine nucleotide exchange factor (SOS). Consequent activation of cytoplasmic protein kinases, together referred to as the mitogen-activated protein kinase (MAPK) signaling cascade, ultimately, stimulates a set of cell cycle regulatory molecules, initiating cell proliferation (See Reference 42). Cell dispersion plays an equally important role in the progression of GBM. Prior evidence shows that integrins co-cluster with growth factor receptor tyrosine kinases such as EGFR and platelet-derived growth factor receptor (PDGFR), initiating intracellular signaling through proteins such as focal adhesion kinase (FAK). SRC kinase binds to ligated integrins and concomitantly binds to and activates FAK resulting in FAK-dependent phosphorylation of downstream substrates, including RhoA. These signaling steps are highly associated with cell motility. Despite our understanding of the biochemical regulation of migration and proliferation in GBM, no mechanism has been deciphered accounting for the control of a cell's differential temporal commitment to migrate or proliferate. Material disclosed in detail in EXAMPLE 1 shows overexpression of Na+/H+ exchanger regulatory factor 1 (NHERF-1) in GBM cells located at the invasive rim compared to cells at the more proliferative tumor core. Principally, NHERF-1 has been characterized as a scaffolding protein capable of recruiting membrane transporters or receptors and/or cytoplasmic signaling proteins into complexes localized at or proximal to the plasma membrane in epithelial cells. NHERF-1 interacts with specific growth factor receptors such as the PDGFR, and possibly EGFR, leading to modulation of mitogenic signaling.

Herein it is demonstrated that NHERF-1 efficiently binds to EGFR and to galectin-1 in GBM. When NHERF-1 expression is decreased using siRNA in three GBM cell lines, cell migration is retarded and cell proliferation accelerates. Signal transduction changes accompany these outcomes. Overexpression of NHERF-1 results in a less proliferative phenotype, with decreased MAPK signaling, increased cell motility and significantly increased signaling of molecules in the FAK-SRC migration pathway. Moreover, NHERF-1 and Grb2 compete for binding to EGFR resulting in altered intracellular signaling favoring either migration or proliferation. By reducing MAPK signaling through knockdown of Grb2, enhanced migration of GBM was observed. Finally, an inverse correlation between NHERF-1 expression and Ki-67 labeling index was discovered when comparing tumor core and rim. Taken together, these findings suggest a novel mechanism implicating NHERF-1 as a switch capable of pushing GBM cells into migratory and proliferative phenotypes.

Cell Culture Conditions and Extracellular Matrix (ECM) Preparation- Human glioma cell lines SF767, SNB19, and T98G were maintained in minimum essential medium supplemented with 10% heat-inactivated fetal bovine serum in a 37° C., 5% $CO_2$ atmosphere at constant humidity. Laminin from human placenta was used at a concentration of 10 m/ml. Glioma-derived ECM was produced as described in Reference 29.

Immunoprecipitation and Mass Spectrometry Analysis- Glioma cells were lysed in 2× sodium dodecyl sulfate (SDS)- sample buffer (0.25 mol/L Tris-HCL, pH 6.8, 2% sodium dodecyl sulfate, 25% glycerol) containing 10 µg/ml aprotinin, 10 µg/ml leupeptin, and 1 mMol/L phenylmethyl sulfonyl fluoride. The lysates were pre-cleared by adding 30 µl of a 50% protein A-sepharose slurry and agitated for one hour at 4° C. For NHERF-1, galectin-1 or Grb2 immunoprecipitations, the precleared lysates were incubated overnight at 4° C. with rabbit IgG (control) or antibody of interest. The following day, the lysates containing the antibody were incubated with 60 µl of a 50% protein-sepharose slurry for one hour at 4° C. The beads were washed four times with NP40 buffer and boiled in 30 µl of 2×SDS sample buffer for five minutes. All samples were separated by 10% SDS-polyacrylamide gel electrophoresis (PAGE). Either Western blot analyses were performed or proteins were detected using Sypro Ruby stain. Bands of differential Sypro Ruby intensity discerned between control and NHERF-1 enriched analytes were excised using a clean razor blade and cut into 1 mm pieces. Gel pieces were extracted and analyzed by liquid chromatography-tandem mass spectrometry (LC-MS/MS). LC-MS/MS analyses of in-gel digested bands, corresponding to proteins bound to NHERF-1, were carried out using a quadrupole ion trap LCQ Classic mass spectrometer. The LCQ Classic is equipped with a Michrom MAGIC 2002 HPLC and a nano-electrospray ionization source. Peptides were eluted from a 15 cm pulled tip capillary column (100 µm I.D.×360 mm O.D; 3-5 µm tip opening) packed with 8-9 cm Vydac C18 material (5 micron, 300A pore size), using a gradient of 0-65% solvent B (98% methanol/2% water/0.5% formic acid/0.01% trifluoroacetic acid) over a 60 minute period at a flow rate of 200-300 nl/minute. The sequences of individual fragments were identified using the Turbo SEQUEST algorithm to search and correlate the MS/MS spectra with amino acid sequences in a non-redundant protein database.

Western Blot Analysis—Immunoblotting and protein determination experiments were preformed as in Reference 41. Briefly, monolayers of cells were washed in phosphate buffered saline (PBS) containing 1 mM phenylmethylsulfonyl fluoride (PMSF) and then lysed in 2× sodium dodecyl sulfate (SDS) sample buffer (0.25 M Tris-HCl, pH 6.8, 2% SDS, and 25% glycerol) containing protease inhibitors as described above. Protein concentrations were determined using the BCA assay procedure, with bovine serum albumin as reference. Fifteen micrograms of total cellular protein was loaded per lane, separated by 10% SDS-PAGE and then transferred to nitrocellulose by electroblotting. The nitrocellulose membrane was blocked with 5% non-fat dry milk in tris-buffered saline (pH 8.0) with 0.1% Tween-20 prior to addition of the primary antibody and then HRP-conjugated anti-mouse/rabbit IgG. Bound secondary antibodies were detected using a chemiluminescence system. The following antibodies were all used at a concentration of 1:1000; NHERF-1, galectin-1, phospho-FAK, RhoA, phospho-ERK1/2 and β-actin, EGFR, phospho-SRC, SRC, ERK1/2 and Grb2.

Immunofluoresence Microscopy—T98G cells (n=800) overexpressed with NHERF-1-GFP (green fluorescent protein) plasmid vector were cultured on glass slides for 24 hours then fixed with 4% paraformaldehyde. Cells were permeabilized with 0.5% Triton X-100 for 10 minutes, blocked with 2.5% fetal bovine serum for five minutes, then stained with a galectin-1antibody at a 1:100 dilution followed by a Cy3-conjugated rabbit polyclonal. Slides were counterstained with DAPI and coverslipped using ProLong Gold anti-fade reagent. Cells were viewed using a 40× Zeiss oil immersion objective on a Zeiss LSM 510 inverted confocal microscope.

NHERF-1 Expression Plasmids, siRNA Preparation and Transfections- Plasmid encoding NHERF-1 -GFP was previously described in Reference 52. An siRNA oligonucleotide specific for GL2luciferase was previously described and used as an unrelated siRNA control. Oligonucleotides specific as siRNA sequences against NHERF-1 and Grb2 were designed and validated: NHERF-1-1(target sequence: CAG AAG GAG AAC AGT CGT GAA; SEQ ID NO. 3), NHERF-1-2 (target sequence: AGC GAG GAG CTG AAT TCC CAA; SEQ ID NO. 4), Grb2-1(target sequence: AAG TTT GGA AAC GAT GTG CAG; SEQ ID NO. 5) and Grb2-2 (target sequence: CAA GAA CTA CAT AGA AAT GAA; SEQ ID NO. 6). Transient transfections of both NHERF-1 plasmid vector and siRNA were carried out using Effectene and Lipofectamine 2000 respectively according to manufacturers' protocols. Cells were plated in a 60 mm plate at 5.0×105 cells/plate in 3 ml of DMEM, supplemented with 10% serum without antibiotics. Transfections were carried out according to the manufacturers' protocols after cells were fully adherent (six hours post-plating). Cells were transfected with 2µof NHERF-1 plasmid vector or a concentration of 20 nM NHERF-1 siRNA oligonucleotides for 16 hours. Minimal cell toxicity was observed using these concentrations. Cells were assayed on day two post-transfection.

Radial Cell Migration Assay—Quantification of cellular migration was performed using a microliter scale migration assay. 10-well slides were coated with 10 µg/ml of human laminin at 37° C. for one hour and washed with PBS to enhance cell attachment, while promoting migration. Approximately 2000 cells were plated onto each well of slides using cell sedimentation manifolds to establish a confluent 1 mm diameter monolayer. Cells transfected with siRNA or plasmid vectors were treated in monolayer prior to transfer into manifolds. After sedimentation and adhesion, cells were allowed to disperse up to 48 hours. Measurements were taken of the area occupied by the cells at regular intervals over 48 hours. The average radial migration rate of five replicates was calculated as the increasing radius of the entire cell population over time.

Cell Proliferation Assay—The Alamar Blue assay was used to assess cell. 4000 cells of each population were seeded in quadruplicate wells of 96-well plastic plates in 200 µl of culture medium supplemented with 10% fetal bovine serum. Cells transfected with siRNA or plasmid vectors were treated in monolayer prior to transfer into 96-well plates. After 48 hours, Alamar Blue was then added to the cells in a volume of 20 µl (10% of total volume) per well and the plates were incubated for 4-6 hours at 37° C. The plates were read on a fluorescence plate reader (excitation, 540 nm; emission, 600 nm). Averages of the fluorescence values were calculated and normalized to controls.

Tissue Microarray (TMA)/Immunofluorescence Staining/ Image Acquisition and Analysis—Sections from a glioma invasion TMA were immunofluorescently stained using an anti-Ki-67 antibody or an anti-NHERF-1 antibody. Image acquisition and analysis were performed. Ratios of immunopositivity at the rim/core were derived from Ki-67 or NHERF-1 AQUA scores of the GBM tissue samples on the tissue microarray. For each TMA spot, areas of tumor are distinguished from stromal elements by creating an epithelial mask (GFAP) from the NHERF-1 or Ki-67 protein signal, which was visualized via the Alexa 488 fluorophore. NHERF-1 or Ki-67 positivity was determined by gating the pixels, in which an intensity threshold was set by visual inspection of TMA spots, and each pixel was recorded as "tumor" or "non-tumor" by the software on the basis of the threshold. The DAPI image, used to designate the nuclei, was subjected to a rapid exponential subtraction algorithm that improves signal-to-noise ratio by subtracting the out-of-focus image from the in-focus image. After application of the exponential subtraction algorithm, the signal intensity of the target protein that was acquired under the Cy5 signal, was scored on a scale of 0-255. These ratios were analyzed against one another to determine a Pearson correlation coefficient.

Identification of Galectin-1 as a NHERF-1-Binding Partner—To identify proteins that interact with NHERF-1, NHERF-1 was immunoprecipitated from T98G cell lysate using a NHERF-1-specific antibody and co-precipitated proteins identified by mass spectrometry. FIG. 1A shows a representative SDS-PAGE stained with Sypro Ruby. A 15-kDa band from the IP lane was excised, the protein was analyzed by LC MS/MS and the sequence was identified as human galectin-1, yielding three tryptic peptides covering 51.9% (by amino acid content) of the protein (FIG. 1B). The interaction of galectin-1 with NHERF-1 was shown using pulldown assays. Galectin-1 was immunoprecipitated from T98G cell lysate using a NHERF-1 antibody in addition to reciprocal experiments co-precipitating NHERF-1 from GBM cell lysates using a galectin-1 antibody (FIGS. 1C and 1D). FIG. 1E shows GBM cells transfected with a NHERF-1-GFP plasmid and then stained with an antibody to galectin-1 followed by a DAPI counter-stain. No signal was detected for galectin-1 when T98G cells were incubated with secondary antibodies alone. Immunohistochemical analysis confirmed that galectin-1 and NHERF-1 co-localize primarily in the membrane and in cytoplasmic regions of the cells, providing additional evidence of a possible physiological interaction.

NHERF-1 Participates in EGFR Signaling and Mediates Downstream Effectors Involved in Cell Migration and Stress Fiber Formation—Immunoprecipitations were performed on T98G cell lysates incubated with a NHERF-1 antibody followed by Western blot analysis probing for EGFR. NHERF-1 does in fact associate with EGFR; control lysate incubated with rabbit IgG rather than a NHERF-1 antibody was negative for EGFR (FIG. 2A). Furthermore, immunoprecipitations were performed to identify the mechanism by which NHERF-1, with the aid of galectin-1, signals downstream of EGFR. Galectin-1 binds to phospho-focal adhesion kinase (pFAK), although NHERF-1 does not (FIGS. 2B and 2C). Moreover, depletion of NHERF-1 in three GBM cell lines caused a significant decrease in phospho-SRC and active RhoA (FIGS. 2D and 2E). These molecules are located throughout a well-defined pathway involved in migration and the formation of cytoskeletal stress fibers.

Overexpression of NHERF-1 Increases GBM Cell Migration Rate and Alters Signaling Related to Migration and Proliferation—SF767, SNB19 and T98G GBM cells were transfected with either GFP-tagged empty vector or a NHERF-1-GFP vector; NHERF-1 overexpression was confirmed by Western blot. When NHERF-1 is overexpressed in these cell lines, there is a marked increase in cell migration (FIG. 3A). Overexpression of NHERF-1 leads to an increase in phospho-SRC, which results in a migratory phenotype. Correspondingly, cells transfected with NHERF-1 decrease phospho-ERK1/2, which plays a major role in a proliferation/cell-cell adhesion pathway (FIG. 3B). Western blot analysis for total SRC and ERK1/2 confirmed that there were no changes in overall levels of the proteins, and that the effect was a diminution of the phosphorylated state (FIG. 3B). These findings indicate that NHERF-1 acts as a molecular switch, that when present at the membrane drives the cell to migrate and to also defer proliferative signaling.

Knockdown of Grb2 Results in an Increase in NHERF-1 Binding to EGFR—The findings depict NHERF-1 as a switch that suppresses proliferation and promotes migration signaling pathways downstream of EGFR. We have shown earlier that NHERF-1 associates with EGFR in GBM; however it is unknown whether this association is direct or indirect. Two independent sequences of siRNA, designed specifically to inhibit Grb2 expression, were introduced into SF767, SNB19 and T98G glioma cells; Grb2 knockdown was validated by Western blot (FIG. 4A). Expression of either NHERF-1 or Grb2 was suppressed by siRNA in T98G glioma cells. Cells transfected with NHERF-1 siRNA were lysed and immunoprecipitated using a Grb2 antibody. Cells transfected with Grb2 siRNA were lysed and immunoprecipitated using a NHERF-1 antibody. Cell lysates were also immunoprecipitated using a rabbit IgG as a control. Western blot analysis was performed on these IP samples and probed for EGFR. When Grb2 expression was suppressed, there was an increase in NHERF-1 binding to EGFR. Moreover, when NHERF-1 expression was suppressed, there was a distinct increase in Grb2 binding to EGFR (FIG. 4B). These results show that there is direct competitive binding between NHERF-1 and Grb2 to EGFR. If NHERF-1 out-competes Grb2 for binding to EGFR, there would be a propensity for the cells to initiate migration. Alternatively, if Grb2 out-competes NHERF-1 for binding to EGFR, the cells would most likely be driven to a more proliferative state.

Depletion of Grb2 in Glioma Cells Enhances Migration in vitro—Monolayer radial migration assays revealed that suppression of Grb2 expression in SF767, SNB19 and T98G glioma cells significantly increased the rate of migration relative to mock-transfected cells (FIG. 5).

Alterations in GBM Proliferation Rate Based on NHERF-1 Expression—When NHERF-1 is overexpressed or Grb2 is inhibited, glioma cells migrate at an increased rate compared to control (FIG. 3A and FIG. 5). Using SF767, SNB19 and T98G cells, either NHERF-1 or Grb2 expression was inhibited using siRNA followed by proliferation rate analysis. When NHERF-1 is inhibited, there is a modest increase in proliferation (FIG. 6A). Grb2 is associated upstream within the RAS-RAF-ERK1/2 proliferation pathway. As a result, inhibiting Grb2 should result in a decreased proliferation rate. As predicted, knockdown of Grb2 did indeed result in decreased proliferation in the cell lines tested (FIG. 6A). In addition, when NHERF-1 is overexpressed in the same three GBM cell lines, there is a marked decrease in proliferation, possibly due to NHERF-1 driving the cells to a more migratory phenotype rather than a proliferative one (FIG. 6B).

NHERF-1 is Inversely Correlated to Ki-67 Expression in an Invasive Brain Tumor Tissue Microarray—NHERF-1 and Ki-67 (nuclear proliferation marker) protein expression from a series of primary human glioblastoma specimens assembled on a tissue microarray prepared from punches of tumor core, edge and far rim from 45 verified GBM cases; sections from the TMA retained 38 instances containing matched core and rim. Following immunofluorescence, AQUA scores of NHERF-1 and Ki-67 within glial fibrillary acidic protein (GFAP) regions-of-interest were derived for matched samples and the ratios of rim over core were calculated. The majority of Ki-67 expression was localized in the cores of the tumors. NHERF-1 expression was found to be greatest in the rims of the tumors, where the tumor cells are most invasive (migratory). When comparing the ratios of rim/core of Ki-67 and rim/core of NHERF-1 AQUA scores, it was found that they are inversely proportional to one another. A Pearson correlation coefficient measured the strength and direction of the linear relationship between NHERF-1 and Ki-67 rim:core AQUA ratios of GBM samples from the tissue microarray where r=0.893.

Involvement of NHERF-1 in GBM Cell Signaling—A molecular diagram representing two diverging pathways guided by relative NHERF-1 and galectin-1 binding as well as speculated interactions based on the preceding data is presented in FIG. 7. The arrows indicate phosphorylation/ activation between pathway molecules, not the strengths of the interaction between the proteins. Phenotypes resulting from activation of these pathways are indicated at the end of each pathway arm.

Figure 17:
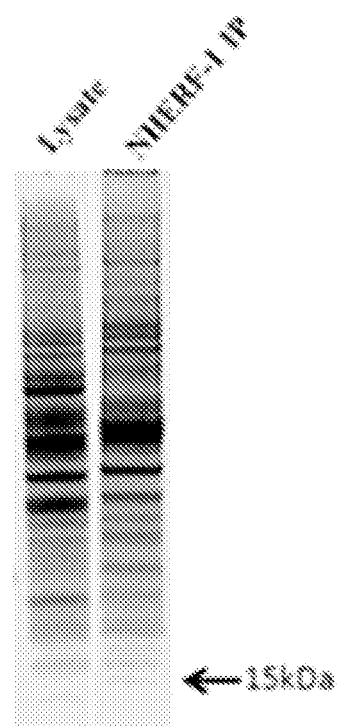
FIG. 17 depicts whole cell lysates incubated with and without anti-NHERF-1 antibody followed by incubation with protein A sepharose beads and controls.
Figure 18:
FIG. 18 depicts sequences from the 15 kDa band indicated by the arrow in FIG. 17, which are SEQ ID NO. 9: SFVLN-LGKDSNNLCLHGNPR; SEQ ID NO. 10: EAVFPFQPGS-VAEVCITFDQANLTVKLPDGYEEK; SEQ ID NO. 11: LNLEAINYMAADGDFK; immunoprecipitation of T98G cell lysates with anti-NHERF-1antibody; and reverse immunoprecipitation of T98G cell lysates using anti-galectin-1 Ab (including controls).
Figure 18:
Figure 19:
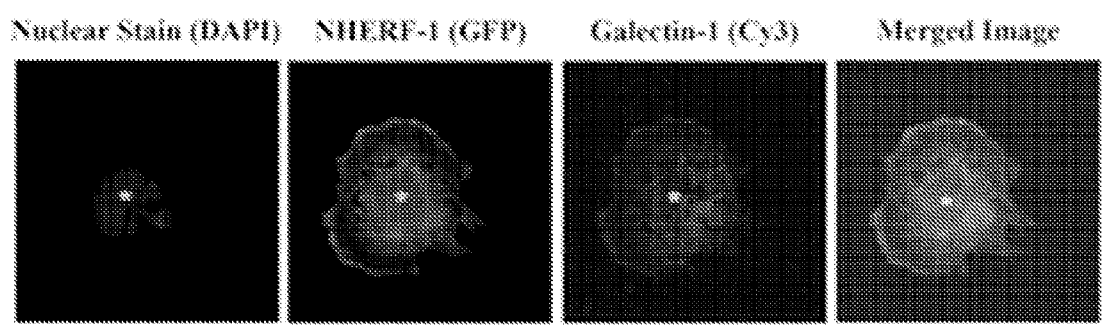
FIG. 19 depicts co-localization of NHERF-1 and galectin 1 in T98G cells by immunofluorescent staining.

In FIG. 17, Protein A-sepharose beads were incubated with pre-cleared whole-cell lysates that had been previously incubated with NHERF-1 antibody or 2μg/ml rabbit IgG. After low-stringency washes, proteins were eluted, size fractioned by SDS-PAGE, stained and visualized. The arrowhead indicates the position of a 15-kDa band effectively enriched by the NHERF-1 antibody. The lysate lane includes proteins that bound non-specifically to beads alone. Note that the 15-kDa band is absent. In FIG. 18 (top), the single prominent 15-kDa band was excised and peptide sequences were obtained by liquid chromatography-tandem mass spectrometry (LC-MS/MS). Three non-continuous peptide fragments covering 51.9% (by amino acid content) of a protein, identified as human galectin-1, were identified (SEQ ID NO. 9: SFVLN-LGKDSNNLCLHGNPR; SEQ ID NO. 10: EAVFPFQPGS-VAEVCITFDQANLTVKLPDGYEEK; SEQ ID NO. 11: LNLEAINYMAADGDFK; see FIG. 18 (top)). In FIG. 18 (middle) Immunoprecipitations (IP) of T98G cell lysates using rabbit anti-NHERF-1Ab (+) or control rabbit IgG (−) were conducted, bound proteins were eluted, size fractioned and transferred to nitrocellulose. Western blot analysis confirmed galectin-1 as a NHERF-1-binding protein. In FIG. 18 (bottom), reverse IPs of T98G cell lysates using rabbit anti-galectin-1 Ab (+) or control rabbit IgG (−) were conducted, bound proteins were eluted, size fractioned and transferred to nitrocellulose. Western blot analysis validated the interaction between galectin-1 and NHERF-1. In FIG. 19, the co-localization of NHERF-1 and galectin-1 by immuno fluorescent staining of T98G cells is shown. Cells were counterstained with DAPI as a nuclear control.

Figure 20:
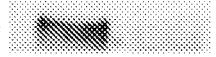
FIG. 20 depicts (top) a Western blot of immunoprecipitates of T98G cell lysates using an anti-NHERF-1 antibody probed with labeled anti-EGFR, (middle) a Western blot of immunoprecipitates of T98G cell lysates using anti-galectin 1 antibody probed with labeled anti-phospho FAK, and (bottom) immunoprecipitates of T98G cell lysates using anti NHERF-1 antibody probed with labeled anti-phospho-FAK.
Figure 20:
Figure 20:
Figure 21:
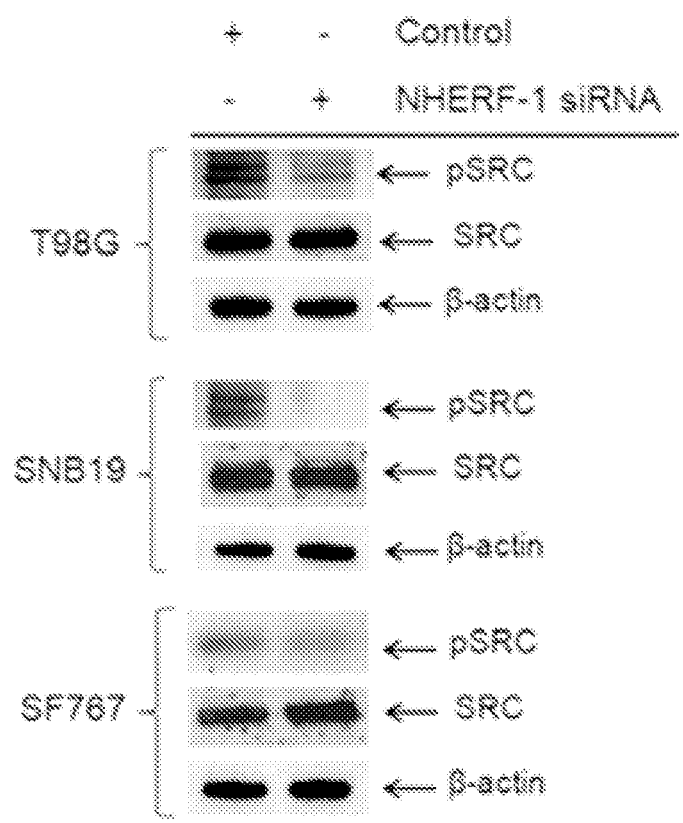
FIG. 21 depicts a Western blot of T98G, SNB19 and SF767 cell lysates transfected with NHERF-1 siRNA and probed with labeled anti-phospho SRC.
Figure 22:
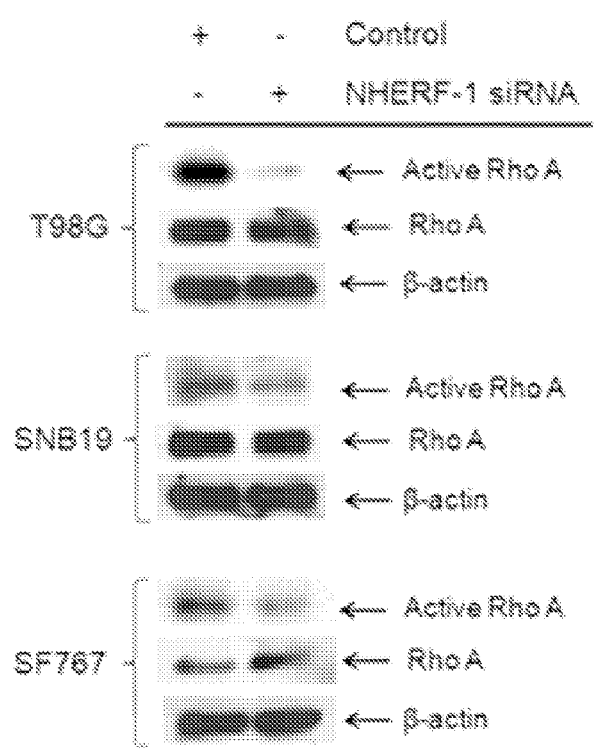
FIG. 22 depicts a Western blot of T98G, SNB19 and SF767 cell lysates transfected with NHERF-1 siRNA and probed with labeled anti-active RhoA.

FIGS. 20-23 show that NHERF-1 modulates a migration-directed molecular signaling pathway. In FIG. 20 (top) IPs of T98G cell lysates using rabbit anti-NHERF-1 Ab (+) or control rabbit IgG (−) were conducted, bound proteins were eluted, size fractioned and transferred to nitrocellulose. Western blot analysis determined EGFR as a NHERF-1-binding protein. In FIG. 20 (middle) IPs of T98G cell lysates using rabbit anti-galectin-1 Ab (+) or control rabbit IgG (−) were conducted, bound proteins were eluted, size fractioned and transferred to nitrocellulose. Western blot analysis determined phospho-FAK as a galectin-1-binding protein. In FIG. 20 (bottom) IPs of T98G cell lysates using rabbit anti-NHERF-1 Ab (+) or control rabbit IgG (−) were conducted, bound proteins were eluted, size fractioned and transferred to nitrocellulose. Western blot analysis determined phospho-FAK is not a direct binding partner of NHERF-1, as opposed to galectin-1. In FIG. 21: Following NHERF-1 knockdown by siRNA in T98G, SNB19 and SF767 cells, Western Blot analysis identified decreases in phospho-SRC. In FIG. 22: Following NHERF-1 knockdown by siRNA in T98G, SNB19 and SF767 cells, Western blot analysis identified decreases in anti-RhoA.

Figure 23:
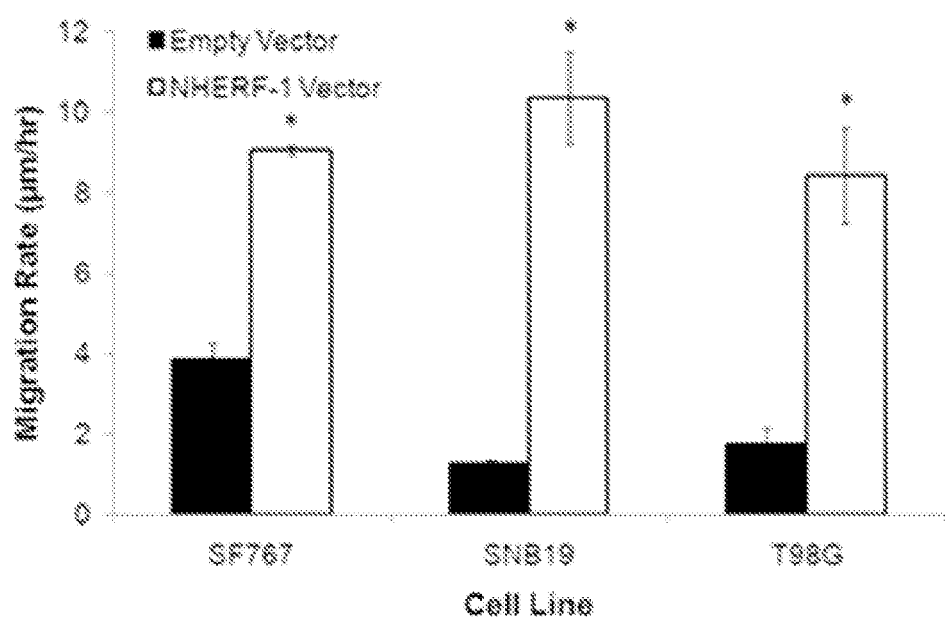
FIG. 23 depicts a graph of migration rates of NHERF-1 transfected cells against controls.
Figure 24:
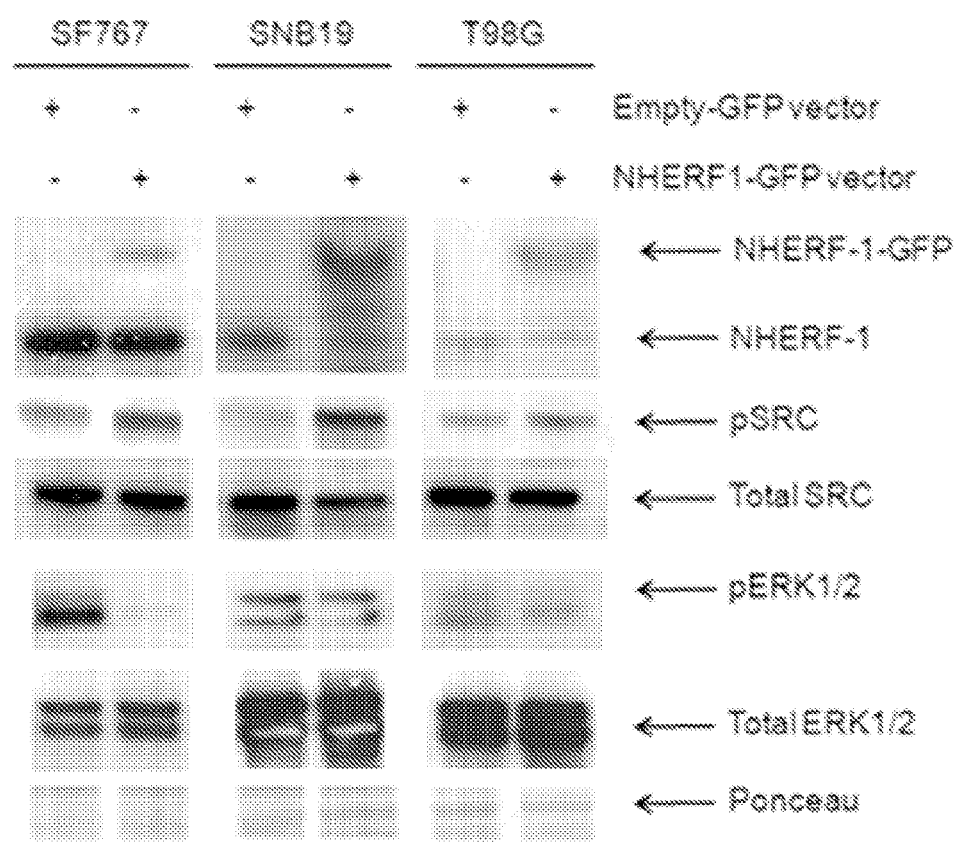
FIG. 24 depicts a Western blot of lysates of SF767, SNB19, and T98G transfected with NHERF-1 or controls probed with labeled anti NHERF-1, anti-phospho-SRC, and anti-labeled ERK1/2.

FIGS. 23 and 24 demonstrate that NHERF-1 confers a pro-migratory phenotype in GBM cells and is a key regulator between pathways that drive proliferation and migration. In FIG. 23: Transfection with NHERF-1-GFP Vector (NV) increased migration of SF767, SNB19 and T98G in a radial migration assay when compared to Empty-GFP Vector (EV)-transfected cells; *P<0.001, comparing EV-transfected cells to NV-transfected cells; 2-tailed Student's t-test. In FIG. 24: Western blot analysis (ponceau stainting used as a loading control) of SF767, SNB19 and T98G cells transfected with either EV or NV confirmed overexpression of NHERF-1. In addition, overexpression of NHERF-1 led to an increase in expression of phospho-SRC and a decreased expression of phospho-ERK1/2. Total SRC and ERK1/2 proteins were evaluated as additional controls.

Figure 25:
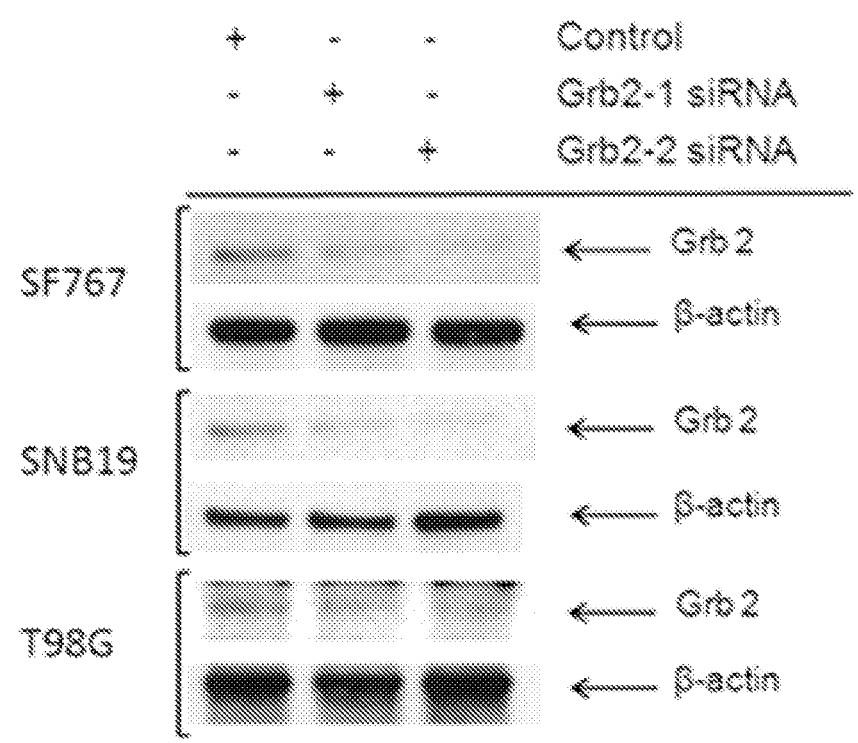
FIG. 25 depicts a Western blot of lysates of SF767, SNB19, and T98G transfected with Grb2 siRNA and probed with labeled anti-Grb2.
Figure 26:
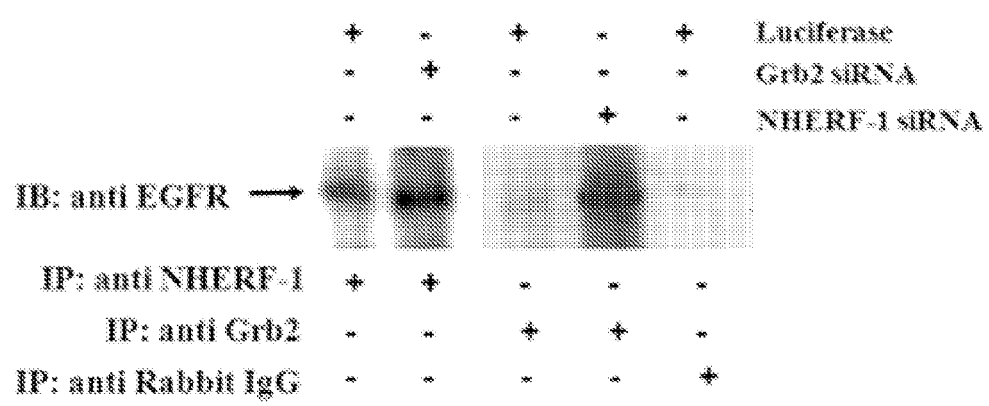
FIG. 26 depicts a Western blot of NHERF-1 and Grb2 immunoprecipitations of lysates of SNB19 cells transfected with Grb2 or NHERF 1 siRNA.

FIGS. 25 and 26 demonstrate that knockdown of Grb2 results in increased NHERF-1 binding to EGFR in GBM cells. In FIG. 24: Western blot analysis (β-actin used as a loading control) confirms a reduction of Grb2 expression in the GBM cell lines SF767, SNB19 and T98G transfected with two Grb2-specific siRNA. Cells transfected with control siRNA (luciferase) are shown for comparison. In FIG. 24: Immunoprecipitation for NHERF-1, Grb2 or rabbit IgG (control) were performed on lysates derived from SNB19 cells transfected with either Grb2 siRNA, NHERF-1 siRNA or a control siRNA (luciferase). Inhibition of NHERF-1 resulted in an increased binding affinity of Grb2 to EGFR. Inhibition of Grb2 demonstrated an increased binding affinity of NHERF-1 to EGFR.

Figure 27:
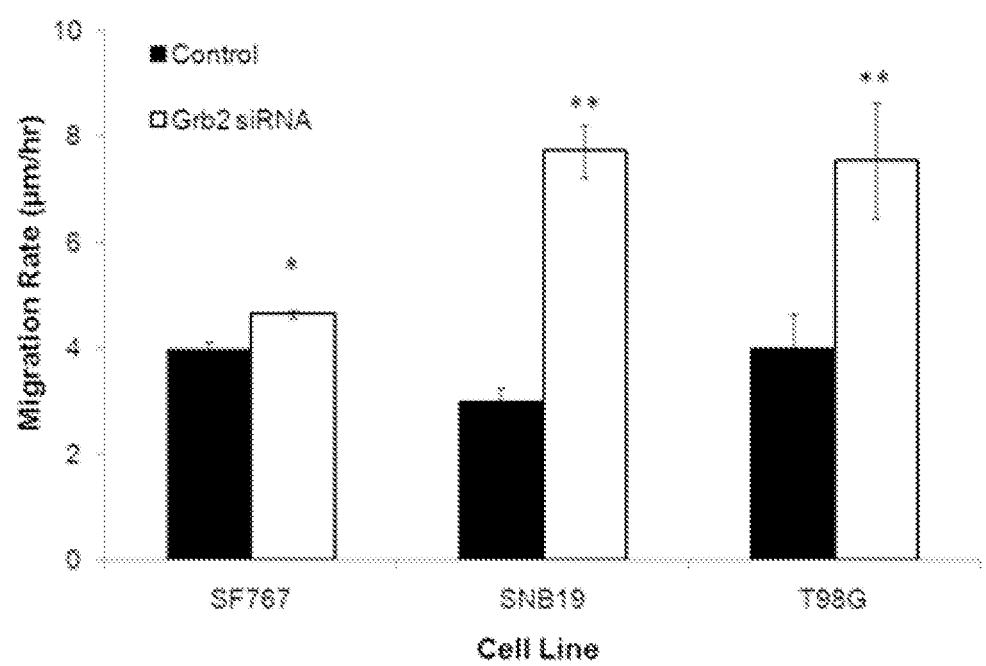
FIG. 27 depicts a graph of radial migration rate in SF767, SNB19, and T98G cell lines transfected with Grb2 siRNA

FIG. 27 demonstrates that inhibition of Grb2 expression results in increased GBM cell migration. SF767, SNB19 and T98G GBM cell lines transfected with Grb2 siRNA resulted in a significant increase in radial migration when compared to cells transfected with a control siRNA (luciferase); *P<0.05, **P<0.001, comparing control-transfected cells to Grb2 siRNA transfected cells; 2-tailed Student's t-test.

Figure 28:
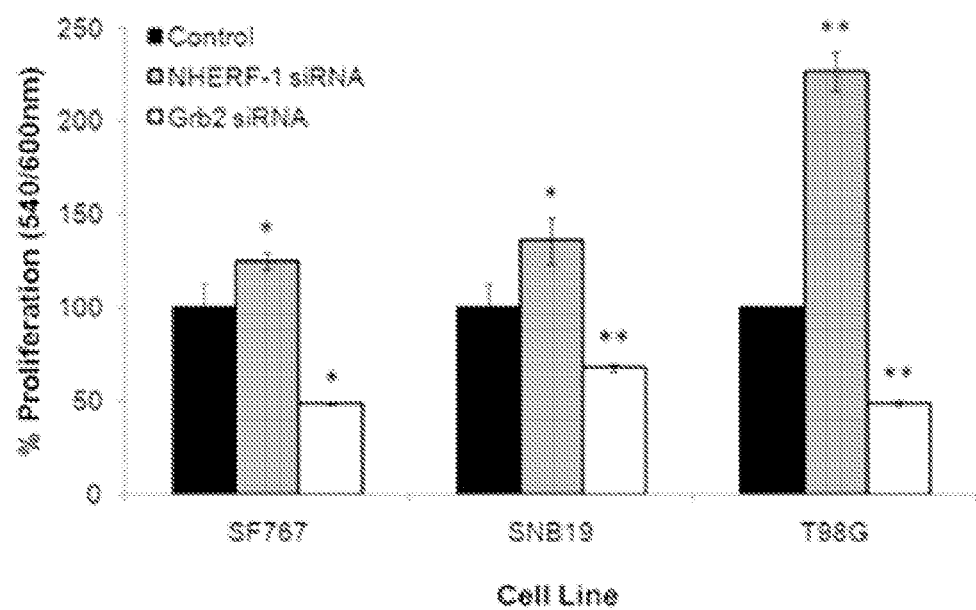
FIG. 28 depicts a graph of the proliferation of SF767, SNB19, and T98G lines after transfection with NHERF-1 or Grb2 siRNA.
Figure 29:
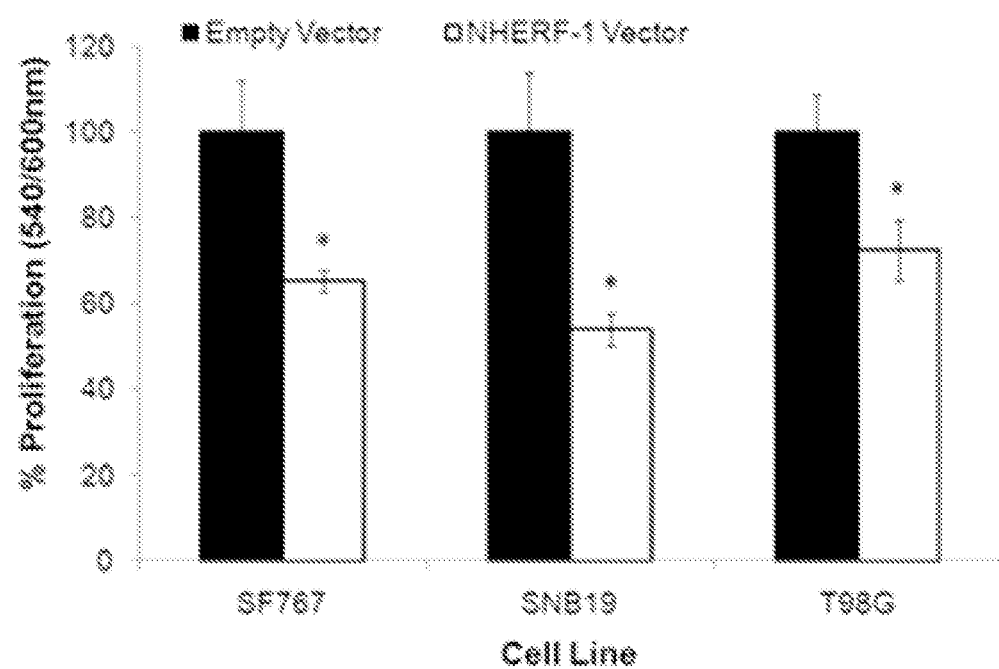
FIG. 29 depicts a graph of the proliferation of SF767, SNB19, and T98G lines overexpressing NHERF-1.

FIGS. 28 and 29 demonstrate that alterations in GBM cell proliferation are consequent to inhibition of Grb2 or NHERF 1 or the overexpression of NHERF-1. In FIG. 28: Viable human glioma cell lines SF767, SNB19 and T98G were quantified 48 hours following knockdown of NHERF-1, Grb2 or control (luciferase) using siRNA; cell growth is reported as percent proliferation based on mean fluorescence intensity of reduced Alamar Blue. Cell proliferation in all cell lines was promoted by knockdown of NHERF-1 and inhibited by knockdown of Grb2; *P<0.01, **P<0.001, comparing control-transfected cells to either NHERF-1 siRNA or Grb2 siRNA-transfected cells; 2-tailed Student's t-test. In FIG. 29, Transfection with NHERF-1-GFP Vector (NV) decreased proliferation of SF767, SNB19 and T98G when compared to Empty-GFP Vector (EV)-transfected cells. After 48 hours, the endpoint was measured as percent proliferation based on mean fluorescence intensity of reduced Alamar Blue; *P<0.001, comparing EV-transfected cells to NV transfected cells; 2-tailed Student's t-test.

Figure 30:
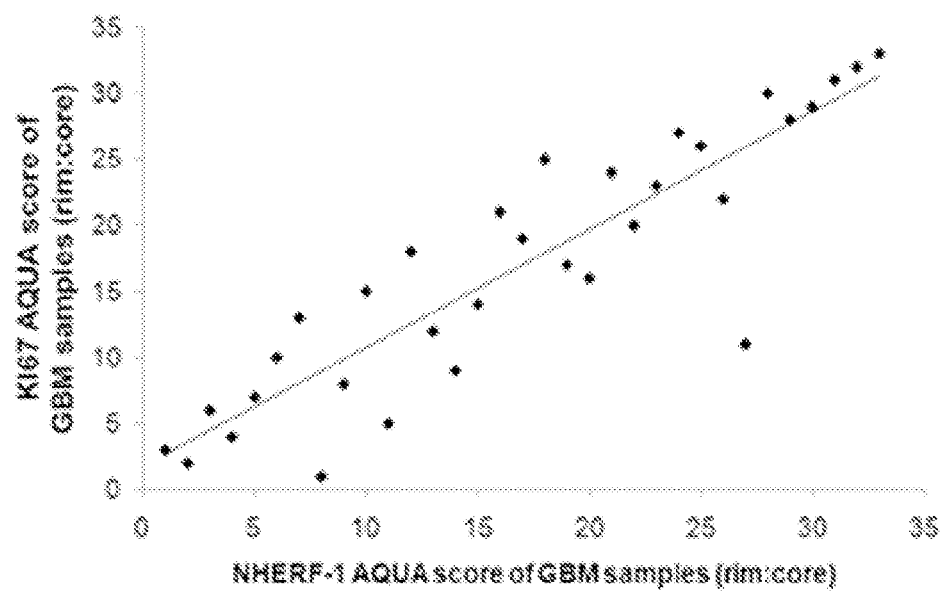
FIG. 30 depicts a Pearson correlation coefficient between Ki-67 and NHERF-1 expression in a GBM invasion tissue microarray.
Figure 31:
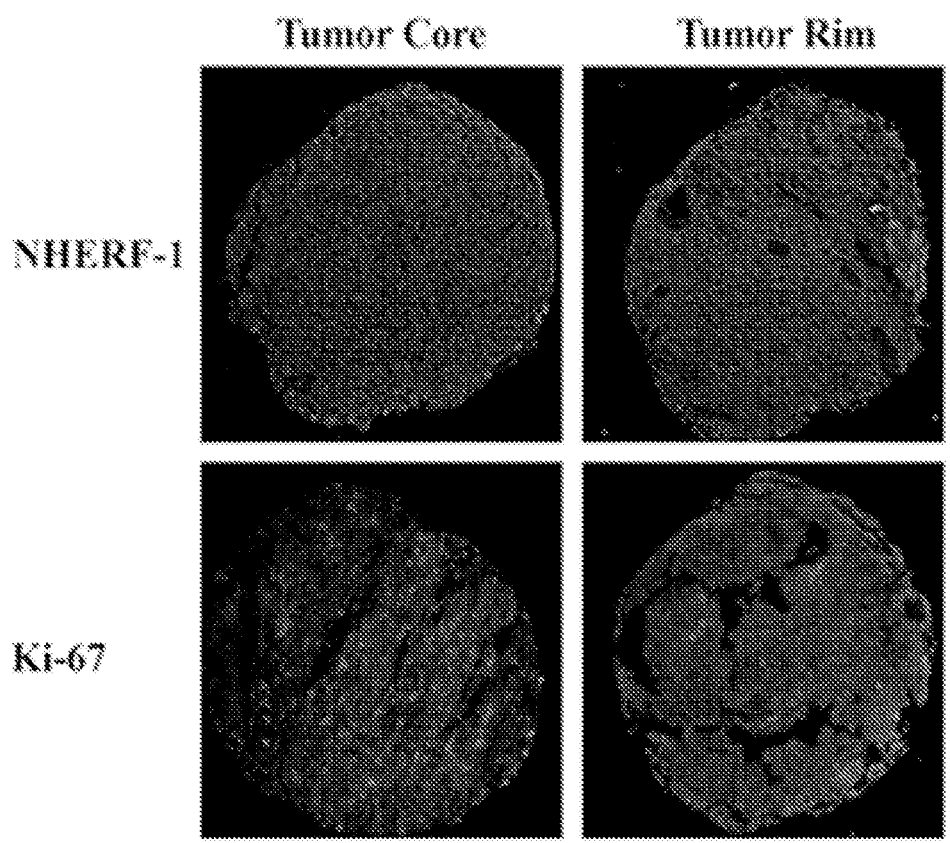
FIG. 31 depicts images from the GBM microarray showing core or rim samples stained with NHERF-1 or Ki-67.

FIGS. 30-31 demonstrate that clinical GBM samples confirm inverse relationship between proliferation and migration based on NHERF-1. In FIG. 30: A Pearson correlation coefficient between Ki-67 and NHERF-1 expression in a GBM invasion tissue microarray. Correlation plot is between AQUA scores of tissue spots taken as a ratio of rim:core for Ki-67 and NHERF-1 tissue microarray datasets. Pearson correlation coefficient; r=0.893. In FIG. 31: Representative images taken from GBM tissue microarray depicting tumor core or rim samples stained with NHERF-1 or Ki-67 (both stained red). Additionally, all tissue samples were stained with GFAP (green) and DAPI (blue) for localization of cell compartments.

Figure 32:
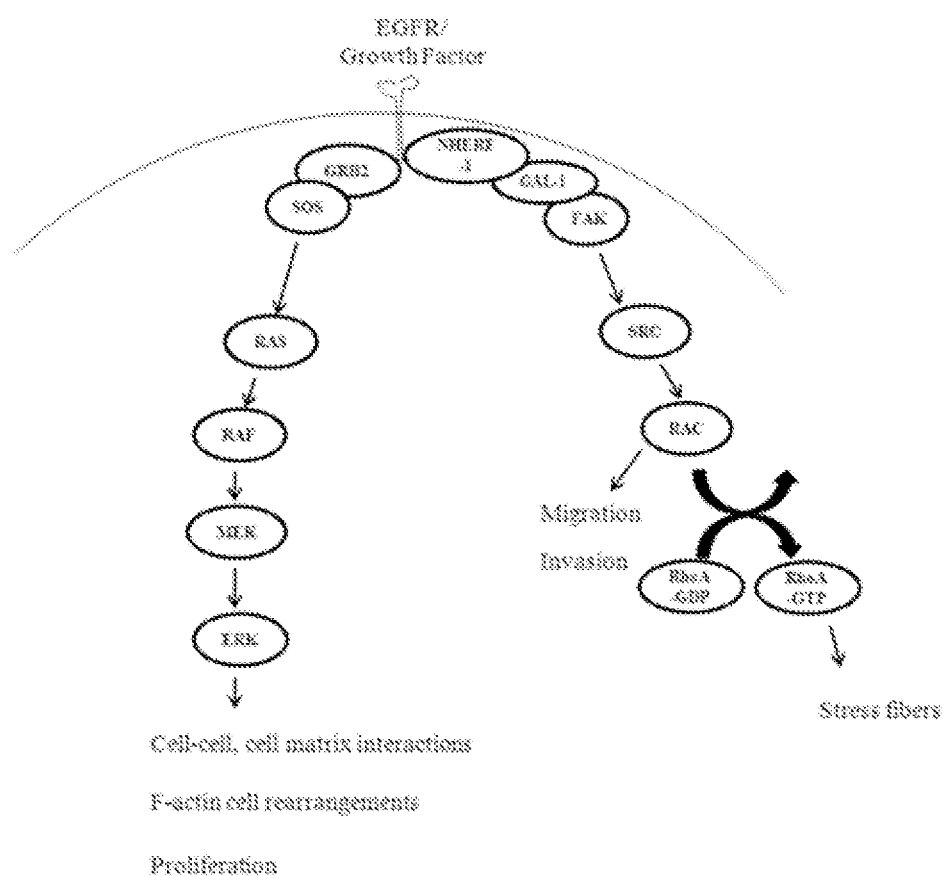
FIG. 32 depicts a model of NHERF-1 regulation of cellular migration.

FIG. 32. Putative model of NHERF-1 regulation of cell migration involving galectin-1. Based on the differential expression of NHERF-1 in rim versus core GBM specimens, NHERF-1 acts as a molecular 'switch' between signaling related to migration or proliferation/survival. NHERF-1 is brought to the plasma membrane by galectin-1 and interacts with EGFR. Furthermore, NHERF-1 competes with Grb2 for binding to EGFR. NHERF-1 has the ability to influence the cell towards a migratory phenotype if overexpressed. When NHERF-1 expression is reduced, migration is halted, allowing Grb2 to bind more effectively to EGFR thereby inducing a more proliferative phenotypic endpoint via the MAPK signaling pathway.

REFERENCES

So as to reduce the complexity and length of the Detailed Specification, Inventors herein expressly incorporate by reference to the extent applicable, all of the following materials.

1. Giese A et al, *J Clin Oncol* 21, 1624-1636 (2003).
2. Keles G E and Berger M S, Semin Oncol 31, 659-665 (2004).
3. Stemmer-Rachamimov A et al, *Am J Pathol* 158, 57-62 (2001).
4. Shenolikar S et al, *Physiology (Bethesda)* 19, 362-369 (2004).
5. Weinman E J et al, *Ann Rev Physiol* 68, 491-505 (2006).
6. Brone B and Eggemont J, *Am J Physiol Cell Physiol* 288, C20-C29 (2005).
7. Nourry C. et al, *Sci STKE* RE7 (2003).
8. Voltz J et al, *J Biol Chem* 282, 33879-33887 (2007).
9. Fraenzer J T et al, *Int J Oncol* 23, 1493-1500 (2003).
10. Shibata T et al, *Hepatology* 38, 178-186 (2003).
11. Bockhorn M et al, *Cancer Res* 64, 2469-2473 (2004).
12. Buttiliglieri S et al, *J Biol Chem* 279, 4136-4143 (2004).
13. Haga A et al, *Int J Cancer* 107, 707-714 (2003).
14. Kinoshita K et al, *Mol Cell Biol* 20, 4680-4690 (2000).
15. Lefranc F et al, *J Clin Oncol* 23, 2411-2422 (2005).
16. Sekharam M et al, *Cancer Res* 63, 7708-7716 (2003).
17. Megalizzi V et al, *Neoplasia* 9, 358-369 (2007).
18. Berens M E et al *Clin Exp Metastasis* 12, 405-415 (1994).
19. Kleihues P and Sobin L H *Cancer* 88, 2887 (2000).
20. Hoelzinger D B et al, *Neoplasia* 7, 7-16 (2005).
21. Mariani L et al, *Cancer Res* 61, 4190-4196 (2001).
22. Louis D N et al, *Acta Neuropathol* 114, 97-109
23. Dolled-Filhart M et al, *Cancer Res* 66, 5487-5494 (2006).
24. HistoRx—AQUA Analaysis Software
25. McCarthy M M et al, *Clin Cancer Res* 11, 5188-5194 (2005).
26. Chuang Y Y et al, *Cancer Res* 64, 8271-8275 (2004).
27. McDonough W S et al, *Neoplasia* 7, 862-872 (2005).
28. Demuth T et al, *Mol Cancer Ther* 6, 1212-1222 (2007).
29. Nakada M et al, *Am J Pathol* 167, 565-576 (2005).
30. Lee A et al *Glia* 55 119-129 (2007).
31. Cardone R A et al, *Mol Biol Cell* 18, 1768-1780 (2007).
32. Friedlander D R et al, *Cancer Res* 1939-1947 (1996).
33. Lipinski C A et al, *Neoplasia* 7, 435-445 (2005).
34. Spruce B A et al, *Cancer Res* 64, 4875-4886 (2004).
35. Eramo A et al, *Cancer Res* 65, 11469-11477 (2005).
36. Green D R and Kroemer G, *Science* 305, 626-629 (2004).
37. Kanzawa T et al, *Cell Death Differ* 11, 448-457 (2004).
38. Decaestecker C. et al, *Med Res Rev* 27, 149-176 (2007).
39. Bridickova N et al, *FEBS Lett* 507, 133 (2001).
40. Rodems K et al, WO/2008/15783, (13 Jun. 2008).
41. Kislin K L et al, *Neoplasia* 11, 377-387 (April, 2009).
42. Blumer K J and Johnson G L, Trends Biochem Sci 19, 236-240 (1994).
43. Sieg D J et al, Nature Cell Biol 2, 249-256 (2000).
44. Wang S E et al Cancer Res 69, 475-482 (2009).
45. Yeo M G et al, Mol Cell Biol 26, 4399-4409 (2006).
46. Eide B L et al, Mol Cell Biol 15, 2819-2827 (1995).
47. Klinghoffer R A et al, Embo J 18, 2459-2471 (1999).
48. Jiang X et al, Mol Biol Cell 14, 858-870 (2003).
49. Lazar C S et al, Mol Biol Cell 5470-5480 (2004).
50. Shevchenko A et al, Anal Chem 68, 850-858 (1996).
51. Yates J R et al, Anal Chem 67, 1426-1436 (1995).
52. Shenolikar S et al, FEBS Lett 489, 233-236 (2001).
53. Wessa P Free Statistics Software, Office of Research Development and Education In., version 1.1.23-r3 Ed. (2009).
54. Giubellino A et al, Expert Opin Ther Targets 12, 1021-1033 (2008).
55. Gotoh N, Cancer Sci 99, 1319-1325 (2008).
56. Lung F D and Tsai J Y, Biopolymers 71, 132-140 (2003).
57. Perrimon N, Curr Opin Cell Biol 6, 260-266 (1994).
58. Wiley H S, Exp Cell Res 284, 78-88 (2003).
59. Camby I et al, Brain Pathol 11, 12-26 (2001).
60. Rorive S et al Glia 3, 241-255 (2001).
61. Camby I et al, J Neuropathol Exp Neurol 61, 585-596 (2002).
62. Halatsch M E et al, Cancer Treat Rev 32, 74-89 (2006).
63. Mischel P S and Cloughsey T F, Brain Pathol 13, 52-61 (2003).
64. Stea B eat al, Cancer Lett 202, 43-51 (2003).
65. Toth J et al, Pathol Oncol Res EPub ahead of print (2008).
66. Viana-Pereira M et al, Anticancer Res 28, 913-920 (2008).
67. Voelzke W R et al, Curr Treat Options Oncol 9, 23-31 (2008).
68. Moiseeva E P et al, J Vasc Res 36, 47-58 (1999).
69. Kairouz R and Daly R J, Breast Cancer Res 2, 197-202 (2000).
70. Pawson T and Scott J D, Science 278, 2075-2080 (1997).
71. van der Geer P et al, Annu Rev Cell Biol 10, 251-337 (1994).

We claim:

1. A method of detecting a presence of invasive glioblastoma in a subject and sensitizing the subject to a therapeutic treatment of invasive glioblastoma that targets non-migrating glioblastoma cells, the method comprising the steps of:

receiving a sample comprising glioblastoma cells from the subject wherein the subject is suspected of having glioblastoma;

adding a first reagent capable of binding to a marker comprising SEQ ID NO. 2 to a mixture comprising the sample;

subjecting the mixture to conditions that allow detection of the binding;

sensitizing the subject by reducing an expression level of the marker comprising SEQ ID NO. 2;

wherein the reduced level of the marker comprising SEQ ID NO. 2 switches invasive glioblastoma cells in the subject to non-migrating cancer cells that are sensitive to a therapeutic invasive glioblastoma that targets the non-migrating glioblastoma cells.

2. The method of claim 1 wherein said first reagent comprises a first antibody and wherein the first antibody comprises a first label.

3. The method of claim 2 further comprising adding a second antibody capable of binding to the first antibody.

4. The method of claim 3 wherein the second antibody comprises a second label.

5. The method of claim 1 wherein the first reagent is affixed to a solid substrate.

6. The method of claim 1 wherein the sample of glioblastoma cells is selected from the group consisting of:
   i. brain tissues;
   ii. fluid samples and single cells.

7. The method of claim 1 comprising the step of collecting a sample from a subject before and after treatment with a therapeutic agent.

8. The method of claim 1 wherein the method of detecting the binding of the first reagent to the marker is selected from the group consisting of enzyme linked immunosorbent assay, immunohistochemistry assay, high pressure liquid chromatography, mass spectrometry, and Western Blot.

9. The method of claim 1 further comprising correlating the presence of an invasive glioblastoma with resistance to a therapeutic that targets non-migrating glioblastoma cells.

10. The method of claim 9 wherein the therapeutic comprises Temozolomide or bevacizumab.

11. The method of claim 1, wherein reducing expression level of the marker comprising SEQ ID NO. 2 is obtained by small inhibitory RNAs targeting the nucleic acid encoding the marker comprising SEQ ID NO. 2.

12. The method of claim 11, wherein the small inhibitory RNAs are selected from the group consisting of SEQ ID NOs. 3, 4, 5 and 6.

* * * * *

SEQUENCE LISTING

<160> NUMBER OF SEQ ID NOS: 11

<210> SEQ ID NO 1
<211> LENGTH: 1077
<212> TYPE: DNA
<213> ORGANISM: Homo sapiens

<400> SEQUENCE: 1

```
atgagcgcgg acgcagcggc cggggcgccc ctgccccggc tctgctgcct ggagaagggt      60
ccgaacggct acggcttcca cctgcacggg gagaagggca agttgggcca gtacatccgg     120
ctggtggagc ccggctcgcc ggccgagaag gcggggctgc tggcggggga ccggctggtg     180
gaggtgaacg gcgaaaacgt ggagaaggag acccaccagc aggtggtgag ccgcatccgc     240
gccgcactca acgccgtgcg cctgctggtg gtcgaccccg agacggacga gcagctgcag     300
aagctcggcg tccaggtccg agaggagctg ctgcgcgccc aggaagcgcc ggggcaggcc     360
gagccgccgg ccgccgccga ggtgcagggg gctggcaacg aaaatgagcc tcgcgaggcc     420
gacaagagcc acccggagca gcgcgagctt cggcctcggc tctgtaccat gaagaagggc     480
cccagtggct atggcttcaa cctgcacagc gacaagtcca gccaggcca gttcatccgg     540
tcagtggacc cagactcccc ggctgaggct tcagggctcc gggcccagga tcgcattgtg     600
gaggtgaacg ggtctgcat ggaggggaag cagcatgggg acgtggtgtc cgccatcagg     660
gctggcgggg acgagaccaa gctgctggtg gtggacaggg aaactgacga gttcttcaag     720
aaatgcagag tgatcccatc tcaggagcac ctgaatggtc ccctgcctgt gcccttcacc     780
aatggggaga tacagaagga gaacagtcgt gaagccctgg cagaggcagc cttggagagc     840
cccaggccag ccctggtgag atccgcctcc agtgacacca gcgaggagct gaattcccaa     900
gacagccccc caaaacagga ctccacagcg ccctcgtcta cctcctcctc cgaccccatc     960
ctagacttca acatctccct ggccatggcc aaagagaggg cccaccagaa acgcagcagc    1020
aaacgggccc cgcagatgga ctggagcaag aaaaacgaac tcttcagcaa cctctga      1077
```

<210> SEQ ID NO 2
<211> LENGTH: 358
<212> TYPE: PRT
<213> ORGANISM: Homo sapiens

<400> SEQUENCE: 2

```
Met Ser Ala Asp Ala Ala Ala Gly Ala Pro Leu Pro Arg Leu Cys Cys
1               5                   10                  15

Leu Glu Lys Gly Pro Asn Gly Tyr Gly Phe His Leu His Gly Glu Lys
                20                  25                  30

Gly Lys Leu Gly Gln Tyr Ile Arg Leu Val Glu Pro Gly Ser Pro Ala
            35                  40                  45

Glu Lys Ala Gly Leu Leu Ala Gly Asp Arg Leu Val Glu Val Asn Gly
        50                  55                  60

Glu Asn Val Glu Lys Glu Thr His Gln Gln Val Val Ser Arg Ile Arg
65                  70                  75                  80

Ala Ala Leu Asn Ala Val Arg Leu Leu Val Val Asp Pro Glu Thr Asp
                85                  90                  95

Glu Gln Leu Gln Lys Leu Gly Val Gln Val Arg Glu Glu Leu Leu Arg
                100                 105                 110

Ala Gln Glu Ala Pro Gly Gln Ala Glu Pro Pro Ala Ala Ala Glu Val
            115                 120                 125
```

-continued

Gln Gly Ala Gly Asn Glu Asn Glu Pro Arg Glu Ala Asp Lys Ser His
130                 135                 140

Pro Glu Gln Arg Glu Leu Arg Pro Arg Leu Cys Thr Met Lys Lys Gly
145                 150                 155                 160

Pro Ser Gly Tyr Gly Phe Asn Leu His Ser Asp Lys Ser Lys Pro Gly
            165                 170                 175

Gln Phe Ile Arg Ser Val Asp Pro Asp Ser Pro Ala Glu Ala Ser Gly
        180                 185                 190

Leu Arg Ala Gln Asp Arg Ile Val Glu Val Asn Gly Val Cys Met Glu
    195                 200                 205

Gly Lys Gln His Gly Asp Val Val Ser Ala Ile Arg Ala Gly Gly Asp
210                 215                 220

Glu Thr Lys Leu Leu Val Val Asp Arg Glu Thr Asp Glu Phe Phe Lys
225                 230                 235                 240

Lys Cys Arg Val Ile Pro Ser Gln Glu His Leu Asn Gly Pro Leu Pro
            245                 250                 255

Val Pro Phe Thr Asn Gly Glu Ile Gln Lys Glu Asn Ser Arg Glu Ala
        260                 265                 270

Leu Ala Glu Ala Ala Leu Glu Ser Pro Arg Pro Ala Leu Val Arg Ser
    275                 280                 285

Ala Ser Ser Asp Thr Ser Glu Glu Leu Asn Ser Gln Asp Ser Pro Pro
290                 295                 300

Lys Gln Asp Ser Thr Ala Pro Ser Ser Thr Ser Ser Ser Asp Pro Ile
305                 310                 315                 320

Leu Asp Phe Asn Ile Ser Leu Ala Met Ala Lys Glu Arg Ala His Gln
            325                 330                 335

Lys Arg Ser Ser Lys Arg Ala Pro Gln Met Asp Trp Ser Lys Lys Asn
        340                 345                 350

Glu Leu Phe Ser Asn Leu
    355

<210> SEQ ID NO 3
<211> LENGTH: 21
<212> TYPE: DNA
<213> ORGANISM: Homo sapiens

<400> SEQUENCE: 3
cagaaggaga acagtcgtga a                                             21

<210> SEQ ID NO 4
<211> LENGTH: 21
<212> TYPE: DNA
<213> ORGANISM: Homo sapiens

<400> SEQUENCE: 4
agcgaggagc tgaattccca a                                             21

<210> SEQ ID NO 5
<211> LENGTH: 21
<212> TYPE: DNA
<213> ORGANISM: Homo sapiens

<400> SEQUENCE: 5
aagtttggaa acgatgtgca g                                             21

<210> SEQ ID NO 6
<211> LENGTH: 21
<212> TYPE: DNA

```
<213> ORGANISM: Homo sapiens

<400> SEQUENCE: 6
caagaactac atagaaatga a                                             21

<210> SEQ ID NO 7
<211> LENGTH: 21
<212> TYPE: DNA
<213> ORGANISM: Homo sapiens

<400> SEQUENCE: 7
ctgcggaatg gatcacactg a                                             21

<210> SEQ ID NO 8
<211> LENGTH: 21
<212> TYPE: DNA
<213> ORGANISM: Homo sapiens

<400> SEQUENCE: 8
aactcattgg gtcagcaatt a                                             21

<210> SEQ ID NO 9
<211> LENGTH: 20
<212> TYPE: PRT
<213> ORGANISM: Homo sapiens

<400> SEQUENCE: 9

Ser Phe Val Leu Asn Leu Gly Lys Asp Ser Asn Asn Leu Cys Leu His
1               5                   10                  15

Gly Asn Pro Arg
            20

<210> SEQ ID NO 10
<211> LENGTH: 34
<212> TYPE: PRT
<213> ORGANISM: Homo sapiens

<400> SEQUENCE: 10

Glu Ala Val Phe Pro Phe Gln Pro Gly Ser Val Ala Glu Val Cys Ile
1               5                   10                  15

Thr Phe Asp Gln Ala Asn Leu Thr Val Lys Leu Pro Asp Gly Tyr Glu
            20                  25                  30

Glu Lys

<210> SEQ ID NO 11
<211> LENGTH: 16
<212> TYPE: PRT
<213> ORGANISM: Homo sapiens

<400> SEQUENCE: 11

Leu Asn Leu Glu Ala Ile Asn Tyr Met Ala Ala Asp Gly Asp Phe Lys
1               5                   10                  15
```